(12) United States Patent
Bernick et al.

(10) Patent No.: US 9,255,245 B2
(45) Date of Patent: Feb. 9, 2016

(54) SAMPLE PROBES AND METHODS FOR SAMPLING INTRACELLULAR MATERIAL

(75) Inventors: Kristin Briana Bernick, San Jose, CA (US); Nicholas M. Sampas, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 481 days.

(21) Appl. No.: 13/541,478

(22) Filed: Jul. 3, 2012

(65) Prior Publication Data

US 2014/0011226 A1 Jan. 9, 2014

(51) Int. Cl.
| | |
|---|---|
| *C12M 1/34* | (2006.01) |
| *C12M 1/00* | (2006.01) |
| *G01Q 60/38* | (2010.01) |
| *B01L 3/02* | (2006.01) |
| *C12M 1/26* | (2006.01) |

(52) U.S. Cl.
CPC ............. *C12M 47/06* (2013.01); *B01L 3/021* (2013.01); *C12M 33/04* (2013.01); *G01Q 60/38* (2013.01)

(58) Field of Classification Search
CPC ...... C12N 15/89; C12M 41/48; C12M 33/04; C12M 21/06; C12M 47/06; B01L 3/021; G01Q 60/38
USPC ............. 435/285.1, 285.2; 250/288; 604/272
See application file for complete search history.

(56) References Cited

U.S. PATENT DOCUMENTS

| | | | | |
|---|---|---|---|---|
| 7,052,652 | B2 * | 5/2006 | Zanzucchi et al. | 422/82.05 |
| 2007/0128083 | A1 | 6/2007 | Yantz et al. | |
| 2008/0302960 | A1 * | 12/2008 | Meister et al. | 250/306 |
| 2012/0019270 | A1 * | 1/2012 | Amodei et al. | 324/692 |
| 2012/0058506 | A1 * | 3/2012 | Gao et al. | 435/29 |

FOREIGN PATENT DOCUMENTS

KR 100384283 B * 5/2003

OTHER PUBLICATIONS

English language machine translation of KR-100384283 (May 16, 2003), pp. 1-13.*
Dorig et al., "Force-Controlled Spatial Manipulation of Viable Mammalian Cells and Micro-Organisms by Means of Fluidfm Technology," Applied Physical Letters, 97, 2010.
Kaigla et al., "A Vertical Microfluidic Probe," Langmuir, 27, 2011, 5686-5693.

(Continued)

*Primary Examiner* — William H Beisner

(57) ABSTRACT

A sample probe includes a tip including a distal end for penetrating a cellular membrane, an opening located at or proximal to the distal end, and tip microchannels extending through the tip and communicating with the opening; and a body adjoining the tip and including body microchannels, wherein at least one of the body microchannels communicates with at least one of the tip microchannels. A method for sampling intracellular material includes inserting a probe tip through a cellular membrane; aspirating intracellular material from the cell, through an opening of the tip, and into a first microchannel of the tip; flowing isolator fluid from a second microchannel of the tip into the first microchannel to form a plug of intracellular material; and aspirating the plug and the isolator fluid through the first microchannel.

8 Claims, 18 Drawing Sheets

(56) References Cited

OTHER PUBLICATIONS

Meister et al., "Fluidfm: Combining Atomic Force Microscopy and Nanofluidics in a Universal Liquid Delivery System for Single Cell Applications and Beyond," Nano Letters, vol. 9, No. 6, 2009, 2501-2507.

Yum et al., "Biofunctionalized Nanoneedles for the Direct and Site-Selective Delivery of Probes Into Living Cells," Biochimica et Biophysica Acta, 1810 (2011) 330-338.

Obataya et al., "Nanoscale Operation of a Living Cell Using an Atomic Force Microscope With a Nanoneedle," Nano Letters, vol. 5, No. 1, 2005, 27-30.

Kihara et al., "Development of a Novel Method to Detect Intrinsic MRNA in a Living Cell by Using a Molecular Beacon-Immobilized Nanoneedle," Biosensors and Bioelectronics, 26, (2010) 1449-1454.

Uehara et al., "Detection of MRNA in Single Living Cells Using AFM Nanoprobes," Methods in Molecular Biology, vol. 544, 2009.

* cited by examiner

US 9,255,245 B2

SAMPLE PROBES AND METHODS FOR SAMPLING INTRACELLULAR MATERIAL

TECHNICAL FIELD

The present invention relates generally to the sampling of biological cells, and more specifically to the addition of fluids into and the extraction of fluids from biological cells.

BACKGROUND

Many tools are available for making multiplex measurements on biological cells in aggregate, but few tools exist to measure the chemistries and compositions within individual cells, particularly live cells and at multiple time points. The methods that do exist are largely based on microscopy and use absorbance or fluorescence of small numbers of markers within cells, and are not capable of making multiplex measurements within complex samples extracted from multiple cells. Measurement of live cells typically involves the immersion of the cells in a liquid medium to maintain the vitality of the cells and keep them in a biologically relevant state for long periods of time. Conditions that are out of the ordinary expose the cells to damage and stresses that confound many biological measurements.

Small-scale capillaries and pipettes have been utilized to inject proteins, peptides, and genetic materials into living cells. However, these techniques are prone to damaging the cells. Moreover, the positioning of capillaries and pipettes is often difficult to accurately control even with the assistance of optical microscopy. Atomic force microscopy (AFM) probe tips, conventionally employed for high-resolution imaging of cell surfaces or force spectroscopy measurements, are being investigated for use as cell probes because AFM force/position feedback signals may be utilized for accurate positioning of the probe and determining when the probe has contacted, indented, and penetrated the cell membrane. For example, an AFM probe tip or a needle formed from an AFM probe tip has been utilized to extract cell components from cells by inserting the AFM probe tip into the cell. Cell components may be retained on the AFM probe tip by physical adsorption to the probe surface or binding to receptors on the probe surface. An AFM probe tip has also been modified to provide a single microfluidic channel capable of dispensing a liquid into a cell. Thus far, however, none of the known probes employed to penetrate cells have been capable of independently injecting material into and extracting fluid from cells utilizing microfluidic channels, or extracting multiple samples from the same cell or multiple cells in a manner in which each sample is isolated from the other samples.

Therefore, there is a need for devices and methods that perform operations on cells while minimizing damage, stress, and unwanted alteration of the cells. There is also a need for devices and methods that enable the independent injection of material into, and extraction of material from, individual cells, as well as other types of single-cell manipulations. There is also a need for devices and methods that enable extraction of multiple samples from cells while keeping each sample isolated from the other samples.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a sample probe includes a tip with at least a distal end configured for penetrating a cellular membrane, an opening located at or proximal to the distal end, and a plurality of tip microchannels extending through the tip and communicating with the opening; and a body adjoining the tip and including a plurality of body microchannels, wherein at least one of the body microchannels communicates with at least one of the tip microchannels.

According to another embodiment, a method for sampling intracellular material includes inserting a tip of a probe through a membrane of a cell; aspirating intracellular material from the cell, through an opening of the tip, and into a first microchannel of the tip; flowing isolator fluid from a second microchannel of the tip into the first microchannel to form a plug of intracellular material defined in part by a boundary between the intracellular material and the isolator fluid; and aspirating the plug and the isolator fluid through the first microchannel.

According to another embodiment, a method for sampling intracellular material includes inserting a tip of a probe through a membrane of a cell, the tip comprising a first microchannel and a second microchannel; injecting a buffer fluid from the second microchannel, through an opening of the tip, and into the cell, wherein the buffer fluid is miscible with the intracellular material and a portion of the intracellular material diffuses into the buffer fluid to form a zone of combined fluid in the cell; aspirating the combined fluid through the opening and into the first microchannel; intermittently flowing isolator fluid from a conduit into the first microchannel to form alternating plugs of combined fluid and isolator fluid, wherein the isolator fluid is immiscible with the combined fluid; and aspirating the alternating plugs through the first microchannel.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
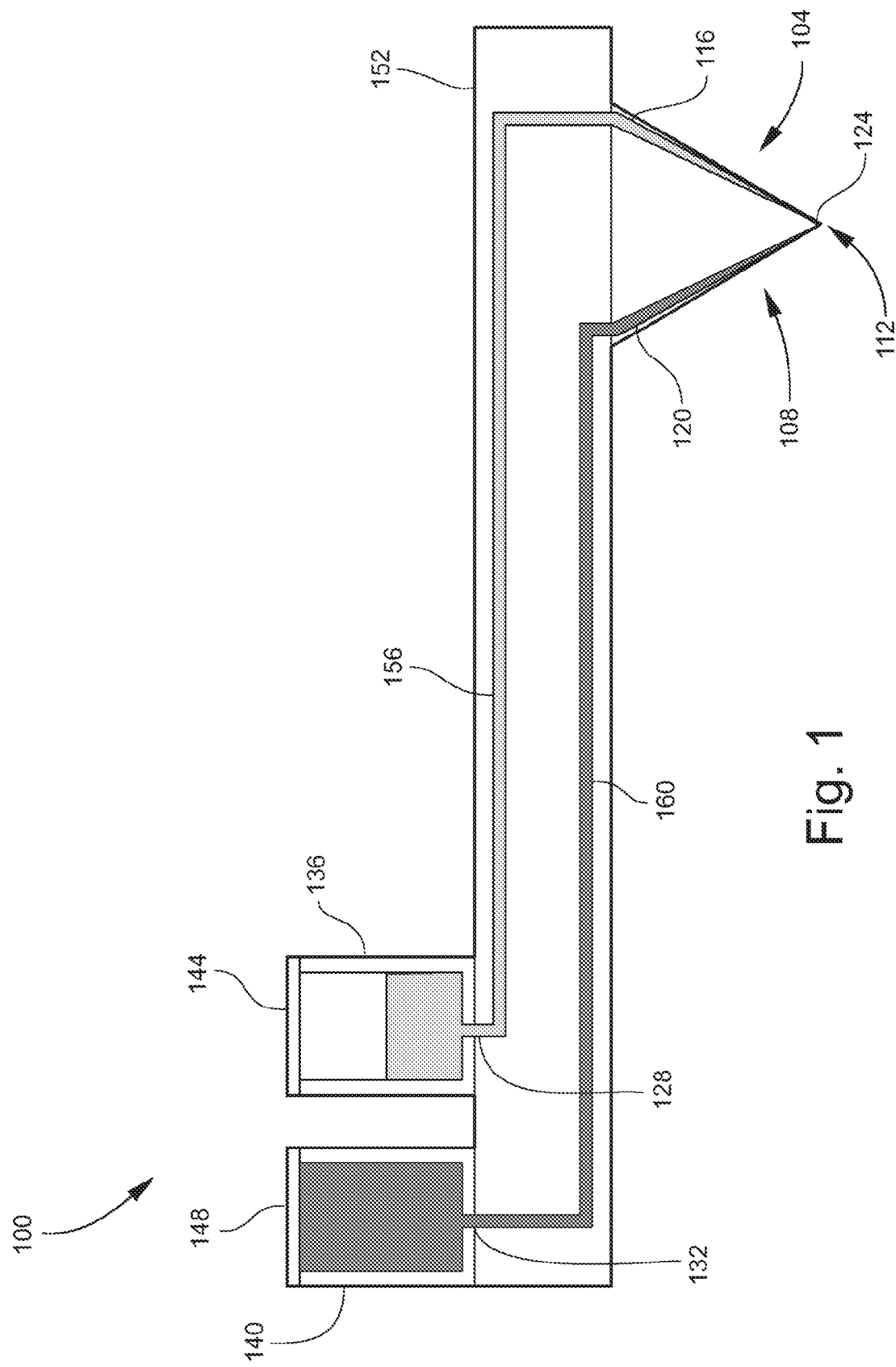
FIG. 1 is a cross-sectional side view of an example of a sample probe according to one embodiment.

As used herein, the term "microfluidic channel" or "microchannel" refers to any type of conduit that defines a flow path for fluid from one end to the other end of the microchannel. In some embodiments, the cross-section (or flow area) of the microchannel has a maximum characteristic dimension on the order of micrometers (e.g., up to about 100 µm) or lower (e.g., nanometers). For example, the maximum characteristic dimension may range from 100 nanometers to 100 µm (0.1 mm). The term "characteristic dimension" refers to a type of dimension that is appropriately descriptive for the shape of the cross-section of the microchannel—for example, diameter in the case of a circular cross-section, major axis in the case of an elliptical cross-section, or a maximum width or height between two opposing sides in the case of a polygonal cross-section. The cross-section of the microchannel may have any of these shapes. Additionally, the cross-section of the microchannel may have an irregular shape, either deliberately or as a result of the limitations of fabrication techniques. The "characteristic dimension" of an irregularly shaped cross-section may be taken to be the dimension characteristic of a regularly shaped cross-section that the irregularly shaped cross-section most closely approximates (e.g., diameter of a circle, major axis of an ellipse, width or height of a polygon, etc.). Flow rates through the microchannel may be on the order of nanoliters per minute, picoliters per minute, or femtoliters per minute.

In the present disclosure, the term "fluid" is used in a general sense to refer to any material that is flowable through a microchannel. For instance, the term "fluid" is not limited solely to liquids or gels but instead may encompass a combination of liquids or gels and solid components carried by liquids or gels.

In typical embodiments, a microchannel is formed in a solid body of material. The material may be of the type utilized in various fields of microfabrication such as microelectronics, microfluidics, micro-electromechanical systems (MEMS), and the like. The composition of the material may be one that is utilized in these fields as a semiconductor, electrical insulator or dielectric, vacuum seal, or structural layer. The material may thus be composed of, for example, a metalloid (e.g., silicon or germanium), a metalloid alloy (e.g., silicon-germanium), a carbide such as silicon carbide, an inorganic oxide or ceramic (e.g., silicon oxide, titanium oxide, or aluminum oxide), an inorganic nitride or oxynitride (e.g., silicon nitride or silicon oxynitride), various glasses, or various polymers. In some embodiments, the material is optically transparent to facilitate the use of optical sensors for various purposes, such as for positioning a sample probe (described below) relative to a sample cell, performing a sample analysis, detecting or identifying a substance flowing through the microchannel, enabling a user of the sample probe to observe flows, etc. The solid body of material may initially be provided in the form of, for example, a substrate, a layer disposed on an underlying substrate, a microfluidic chip, a die singulated from a larger wafer of the material, etc.

The microchannel may be formed in a solid body of material by any technique, now known or later developed in a field of microfabrication, which is suitable for the material's composition and the size and aspect ratio of the microchannel. As non-limiting examples, the microchannel may be formed by an etching technique such as focused ion beam (FIB) etching, deep reactive ion etching (DRIE), or a micromachining technique such as mechanical drilling, laser drilling or ultrasonic milling. Depending on the length and characteristic dimension of the microchannel to be formed, the etching or micromachining may be done in a manner analogous to forming a vertical or three-dimensional "via" partially into or entirely through the thickness of the material (e.g., a "through-wafer" or "through-substrate" via). Alternatively, an initially open channel or trench may be formed on the surface of a substrate, which is then bonded to another substrate to complete the microchannel. The other substrate may present a flat surface, or may also include an initially open channel that is aligned with the open channel of the first substrate as part of the bonding process. The microchannel may be defined (or bounded) directly by one or more walls of a solid body of material. Alternatively, the microchannel may be defined by the inside surface of a tube or capillary, i.e., the tube or capillary wall is the solid body of material in which the microchannel is formed. In the latter case, the tube or capillary may reside in a closed bore or open bore (e.g., a trench, groove or recess) that is formed by one or more walls of another solid body of material.

Depending on its composition, the material defining the microchannel may be biocompatible or chemically inert relative to the fluid flowing through the microchannel. In some embodiments, as part of the fabrication process a suitable coating or surface treatment/functionalization may be applied to the microchannel to impart a desired level of biocompatibility or chemical inertness. In some embodiments, a suitable coating or surface treatment/functionalization may be applied to the microchannel to impart another desired property such as, for example, hydrophobicity or hydrophilicity. Coatings and surface treatments/functionalizations for such purposes are readily appreciated by persons skilled in the art.

As used herein, the term "intracellular material" or "cellular contents" refers to any component contained by the membrane of a biological cell that may be aspirated from the cell in accordance with the present disclosure. Intracellular material or cellular contents may for example, include one or more components of cytoplasm and/or a portion or the entirety of an organelle.

FIG. 1 is a cross-sectional side view of an example of a sample probe 100 according to one embodiment. The sample probe 100 includes a probe tip 104. The probe tip 104 has a distal end 108 that is configured for penetrating a cellular membrane. For this purpose, the probe tip 104 or at least its distal end 108 may have a tapered profile (e.g., a conical or pyramidal profile) that terminates at an apex 112, as in the example illustrated in FIG. 1. In this case, the apex 112 may have a degree of sharpness suitable for penetrating a cellular membrane. The sharpness may be defined by a radius of curvature of the apex 112 ranging from 1 nm to 50 nm. In other embodiments (not shown), the probe tip 104 or its distal end 108 may be provided in the form of an elongated (high aspect ratio) structure such as a needle-like structure. The probe tip 104 includes a plurality of microchannels (or tip microchannels) running through its thickness. In FIG. 1, a first microchannel (or first tip microchannel) 116 and a second microchannel (or second tip microchannel) 120 are illustrated by example with the understanding that additional microchannels may be included. Different microchannels may be utilized for different purposes. For example, one microchannel may be utilized to aspirate fluids into the probe tip 104 while another microchannel is utilized to dispense fluids from the probe tip 104, or different microchannels may be utilized to dispense different fluids from the probe tip 104. The probe tip 104 also includes an opening 124 providing fluid communication between the environment external to the probe tip 104 and one or more of the microchannels 116, 120. The opening 124 may be located at or proximal to the distal end 108. That is, from the perspective of FIG. 1 the opening 124 may be located directly at or very near to the central axis of the probe tip 104, or may be located off-center from the central axis on the outer surface of the probe tip 104 at some elevation above the distal end 108. The opening 124 may be a single opening (or orifice) or may comprise a plurality of discrete openings (or orifices). In the latter case, each opening may communicate with one or more respective microchannels 116, 120. A given opening may serve as an outlet from and/or an inlet into the probe tip 104. A given opening may have a diameter ranging, for example, from 1 nm to 100 nm.

In some embodiments, the cross-section of a given microchannel may taper down to the diameter of a corresponding opening.

The sample probe 100 may also include a port providing fluid communication between the environment external to the sample probe 100 and one or more of the microchannels 116, 120. The port may be located remotely from the opening 124 of the probe tip 104. The port may be a single port or may comprise a plurality of discrete ports. In the latter case, each port may communicate with one or more respective microchannels 116, 120. A given port may serve as an outlet from and/or an inlet into sample probe 100. The port may be configured for making a fluidic connection with any type of fluid-carrying component such as, for example, a tube or capillary, a fluid conduit of a device that holds the sample probe, a reservoir, a pump, or a functional device that performs an operation on the fluid flowing through the microchannel such as reaction, dilution, buffering, mixing, heating, valve operation or metering, measurement, sensing, detection, or analysis. The port may be utilized to supply a fluid that is transported via a microchannel to the opening 124 for dispensing from the probe tip 104, or for collecting a fluid aspirated into the probe tip 104 and transported via a microchannel. The port may couple one or more microchannels with a sample preparation device or a sample analysis device. Such devices may be implemented on microfluidic chips coupled to the port via tubing or other type of conduits.

In the embodiment illustrated in FIG. 1, the port includes a first port 128 communicating with the first microchannel 116 and a second port 132 communicating with the second microchannel 120. The first port 128 communicates with a first reservoir 136 and the second port 132 communicates with a second reservoir 140. FIG. 1 also schematically illustrates a first pump 144 communicating with the first reservoir 136 and a second pump 148 communicating with the second reservoir 140. The pumps 144 and 148 may be any devices suitable for moving fluids in microfluidic applications, and thus may operate on the basis of small-scale positive displacement (e.g., micro-syringe), or a mechanism such as piezoelectric (e.g., driven by a lead zirconate titanate, or PZT, element), ultrasonic, electrostatic, pneumatic, magnetic, hydrodynamic, electro-osmotic, or electrochemical actuation. Depending on the embodiment, the reservoirs 136 and 140 and pumps 144 and 148, may be considered as being adjoined to the sample probe 100 or part of the sample probe 100. In other embodiments, the reservoirs 136 and 140 and pumps 144 and 148 may be located remotely from the sample probe 100 and communicate with the ports 128 and 132 via tubing.

The sample probe 100 may include one or more other structures in addition to the probe tip 104. An additional structure may be provided for various purposes such as, for example, supporting the probe tip 104, extending the length of one or more microchannels of the probe tip 104, or providing a functional device that performs an operation on fluid flowing through a microchannel such as the functional devices noted above. In the embodiment illustrated in FIG. 1, the sample probe 100 includes a body 152 adjoining the probe tip 104. The body 152 may be fabricated separately and thereafter adjoined to the probe tip 104 by an appropriate bonding process, or the body 152 and probe tip 104 may be fabricated together as a monolithic structure. The body 152 may be a block or chip of material that is elongated in a direction transverse to the central axis of the probe tip 104. The body 152 may include a system of microchannels (or body microchannels), one or more of which may communicate with one or more of the tip microchannels 116, 120 and/or one or more of the ports 128, 132. The body microchannels may change the direction of fluid flow one or more times through the body 152. In the illustrated embodiment, the body 152 includes a first body microchannel 156 and a second body microchannel 160. The probe tip 104 is adjoined to a surface of the body 152 where open ends of the body microchannels 156 and 160 are located, such that the first body microchannel 156 communicates with the first tip microchannel 116 and the second body microchannel 160 communicates with the second tip microchannel 120. Also in this embodiment, the ports 128 and 132 are located on the body 152 at a remote distance from where the probe tip 104 is located, and the reservoirs 136 and 140 are adjoined to the body 152. The ports 128 and 132 may be open ends of the respective body microchannels 156 and 160, or may otherwise communicate with the respective body microchannels 156 and 160. Hence, the sample probe 100 defines a flow path between the first reservoir 136 and the opening 124 via the first tip microchannel 116 and first body microchannel 156, and a flow path between the second reservoir 140 and the opening 124 via the second tip microchannel 120 and second body microchannel 160. One or both reservoirs 136, 140 may be utilized as a fluid supply source or a fluid collection receptacle.

The body microchannels 156 and 160 may be formed by a through-via type of technique, or by forming open channels in one or both of two body halves and thereafter aligning and bonding the body halves together, as noted above. It will be understood that the illustrated sample probe 100 may be considered as defining continuous flow paths between the opening 124 of the probe tip 104 and the reservoirs 136 and 140 or other fluid destinations or fluid sources. Accordingly, the sample probe 100 may be considered as providing a microchannel that includes one section in the probe tip 104 (the first tip microchannel 116) and another section in the body 152 (the first body microchannel 156), and another microchannel that includes one section in the probe tip 104 (the second tip microchannel 120) and another section in the body 152 (the second body microchannel 160). That is, in some embodiments the first tip microchannel 116 and the first body microchannel 156 may be considered as being a single microchannel, and the second tip microchannel 120 and the second body microchannel 160 may be considered as being a single microchannel. Moreover, in addition to what is shown by example in FIG. 1, reservoirs or other microfluidic features (not shown) may be formed in the bulk of the body 152 and may be part of (or operate on fluid in) the internal flow paths.

In some embodiments, the sample probe 100 is additionally configured for atomic force microscopy (AFM), in which case the body 152 of the sample probe 100 may be a deflectable cantilever suitable for AFM. The body 152 may be composed of any deflectable material suitable for AFM such as, for example, silicon or silicon nitride. An example of an AFM-based sample probe and associated system is described further below in conjunction with FIG. 18.

Figure 2:
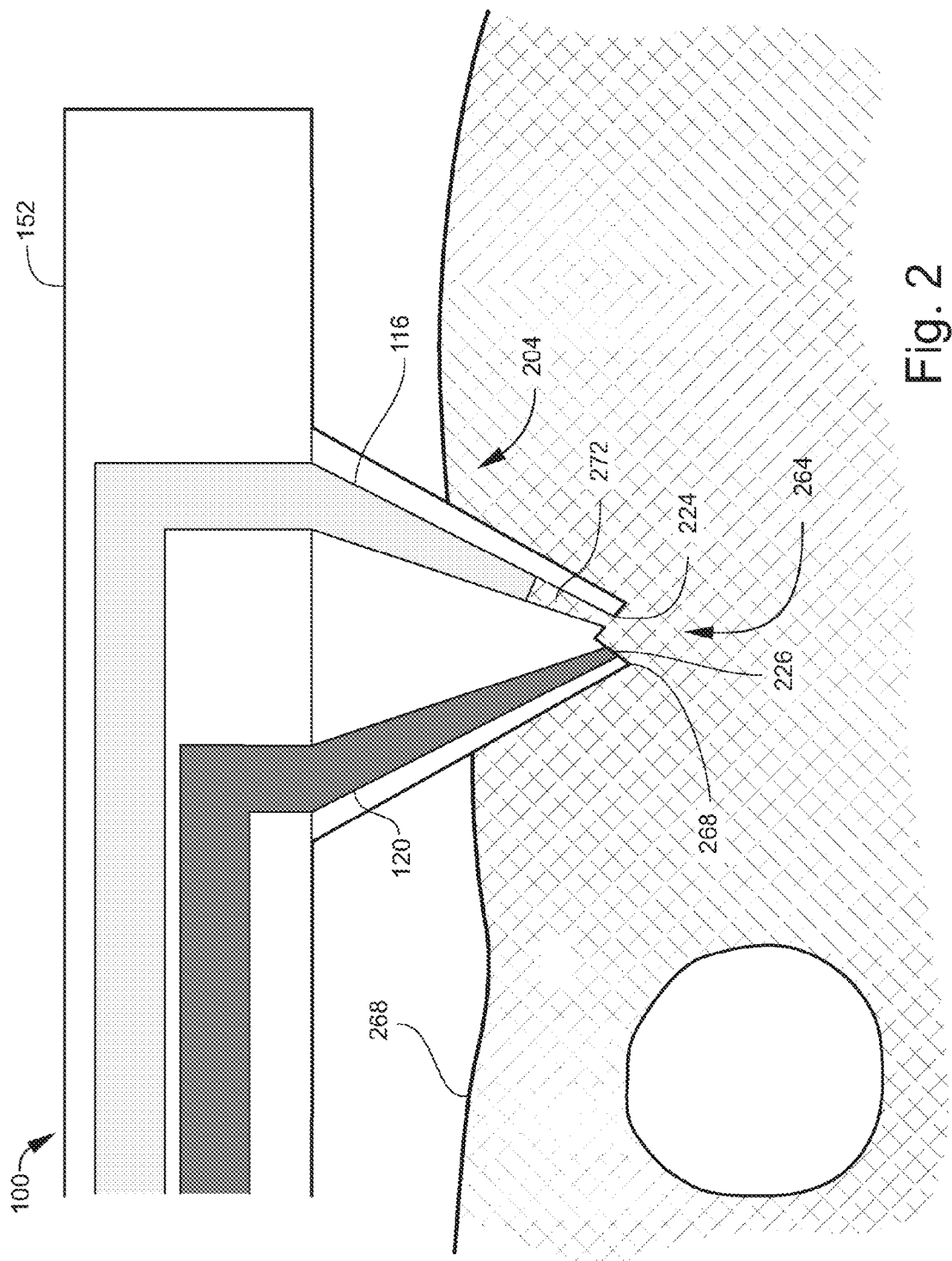
FIG. 2 is a zoomed in cross-sectional side view of an example of a sample probe according to one embodiment of tip geometry.

FIG. 2 is a cross-sectional side view of the sample probe 100 that includes an example of a probe tip 204 according to one embodiment. At the distal end, a cavity 264 is formed into the thickness of the probe tip 204 such that the distal end includes an annular apex 268 coaxial about the central axis. The cavity 264 may be any inverted or concave profile such as, for example, a conical, hemispherical, semielliptical, parabolic, or hyperbolic profile. In the illustrated embodiment, the opening of the probe tip 204 includes a first opening or orifice 224 communicating with the first microchannel 116 and a second opening or orifice 226 communicating with the second microchannel 120. In the illustrated embodiment both openings 224 and 226 are located at the cavity 264, although in other embodiments one or both openings 224, 226 may be located outside of the cavity 264 on the outside surface of the probe tip 204.

The sample probe 100 may be utilized for independent injection of material into, and extraction of material from, individual living cells. The distal end of the probe tip 204 as described above is configured for enabling the probe tip 204 to penetrate a membrane 268 of a cell 270 with minimal force and minimal stress and damage to the cell 270. The sample probe 100 may be utilized to sample (aspirate) and store intracellular material from multiple cells, as well as multiple samples of intracellular material from the same cell, for downstream measurement and analysis. The probe tip 204 is useful for operations on living cells because it may be repeatedly inserted into the same cell or different cells without needing to remove the sample probe 100 from an associated holding apparatus (not shown) and, in the case of multiple cells provided in the same volume of culture medium, without needing to remove the probe tip 204 from the culture medium. The probe tip 204 may be moved from one cell to the next by utilizing any suitable multi-axis staging device (not shown). The staging device may include a device that supports the cells (or supports a cell holder such as a glass slide, dish or multi-well plate) and is configured to move the cells relative to the probe tip 204. Alternatively or additionally, the staging device may include a device that supports the sample probe 100 and moves the probe tip 204 relative to the cells. Moreover, multiple sample plugs may remain isolated from each other while being flowed through or stored in the same microchannel by utilizing an isolator fluid as described below. Also, the sample probe 100 may minimize or eliminate potential sample contamination from nucleic acids and proteins present in a culture medium, enabling cells to be operated on without needing frequent washes and media changes that have the potential to alter the state of the cell.

An example of a method for sampling intracellular material will now be described with reference to FIGS. 2-7. Referring to FIG. 2, the sample probe 100 is moved to a selected cell 270 and lowered toward the cell 270 until the distal end of the probe tip 204 has penetrated the cell membrane 268. The probe tip 204 may be aligned over the cell 270 such that, upon penetration, the distal end is located in a specific area of the cell interior containing a specific component of intracellular material to be aspirated. Intracellular material 272 is aspirated through the first opening 224 and into the first microchannel 116, such as by operating the first pump 144 shown in FIG. 1.

Figure 3:
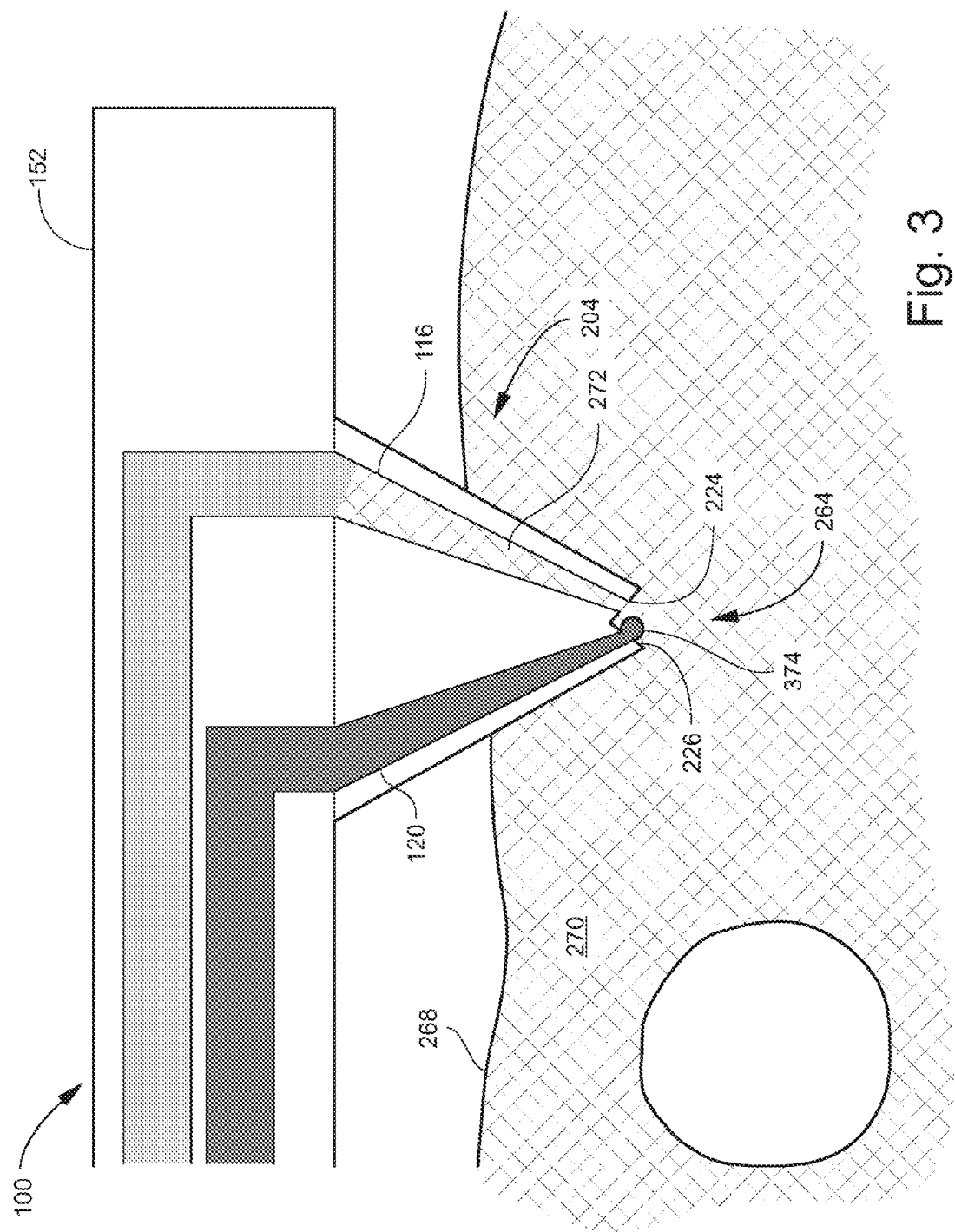
FIG. 3 is a cross-sectional side view of the sample probe illustrated in FIG. 2, wherein the sample probe is operated to aspirate intracellular material from the cell and begin injecting isolator fluid to separate sample plugs of cellular material, according to an example of a method disclosed herein.

Referring to FIG. 3, while the intracellular material is being aspirated, an interior fluid may be injected from the second microchannel 120, through the second opening 226 and into the cell interior, such as by operating the second pump 148 shown in FIG. 1. The isolator fluid may be a fluid that is immiscible with the intracellular material. The immiscibility of the isolator fluid will depend on the composition of the intracellular fluid. As a general matter, for a broad range of applications contemplated by the present disclosure, examples of immiscible isolator fluids include, but are not limited to, non-aqueous fluids such as oils, silicone oils, and mineral oil for biological applications such as those commercially available from Sigma-Aldrich Co. In the present context, the term "immiscible" encompasses the term "substantially immiscible." In the present context, the isolator fluid is substantially immiscible if, in the event some mixing with the intracellular material occurs, the amount of mixing is negligible or inconsequential in the sense that it does not adversely affect the measurements, analysis or fluid manipulation being implemented by the method. In some embodiments, the isolator fluid may be a gas or a liquid in which a gas is entrained.

In some embodiments, the isolator fluid may be miscible or partially miscible with the intracellular material, particularly in a method that is carried out rapidly enough that mixing or diffusion does not appreciably impair the method. As also shown in FIG. 3, as the isolator fluid reaches the cell interior it begins to form a bulb (or globule, bead, blob, etc.) 374 in the cavity 264. Formation of the bulb 374 may be the result of or promoted by any number of factors, such as the surface tension, viscosity, immiscibility and/or hydrophobicity of the isolator fluid. Moreover, the surface of the cavity 264 may promote or be treated to promote bulb formation (e.g., anti-wetting or hydrophobic properties). In some embodiments, surfactants are used to modify the surface tension, and the miscibility of oily isolation fluid or aqueous solutions. Surfactants include, for example, sodium dodecyl sulfate, polyethylene oxide and polypropylene oxide.

Figure 4:
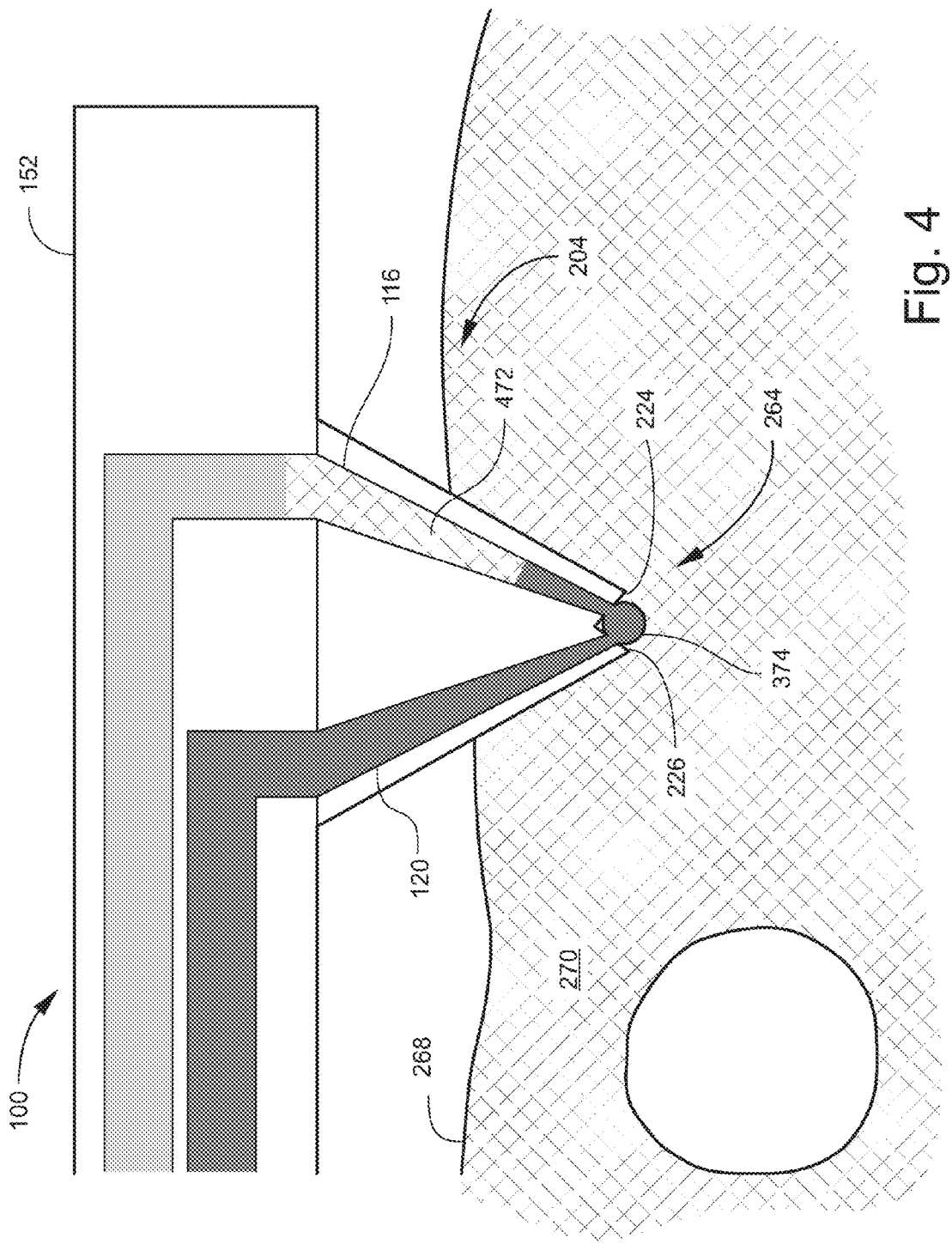
FIG. 4 is a cross-sectional side view of the sample probe illustrated in FIG. 2, and represents the next step in the sampling process, wherein the sample probe is operated to form a sample plug according to the method.

Referring to FIG. 4, while the intracellular fluid continues to be aspirated and the isolator fluid continues to be injected, the bulb 374 increases in volume in the cavity 264 and eventually blocks the first opening 224, thereby isolating the first microchannel 116 from the cell interior and preventing further extraction of intracellular material from the cell interior at this time. However, vacuum continues to be applied in the first microchannel 116, and so the isolator fluid begins to be aspirated into the first microchannel behind the intracellular material already residing in the first microchannel 116. An increased pressure can be achieved to enhance the aspiration of the sample by enclosing and operating the sample and sample probe 100 in a chamber at an elevated pressure. In this manner a plug or aliquot of intracellular material (or sample plug) 472 of a finite volume is formed in the first microchannel 116 and the sample plug 472 and isolator fluid may continue to be aspirated simultaneously in series. The sample plug 472 may be considered as being defined in part by the boundary or interface between the intracellular material and the succeeding isolator fluid. The volume (size) of the sample plug 472 may be controlled by controlling the time at which injection of the isolator fluid starts after the start of aspiration, in view of the flow rates being implemented in the microchannels 116 and 120. The volume of the sample plug 472 may range, for example, from $10^{-13}$ to $10^{-15}$ liters (l). As another example, the plug volume may range from $1 \times 10^{-14}$ l to $5 \times 10^{-14}$ l. The flow rates of fluids in the microchannels 116 and 120 may also be controlled, such as by controlling the pumps 144 and 148 illustrated in FIG. 1, and may be the same or different as needed for a given stage of operation. The fluid flow rate in a given microchannel may range, for example, from $10^{-13}$ l/s to $10^{-17}$ l/s.

Figure 5:
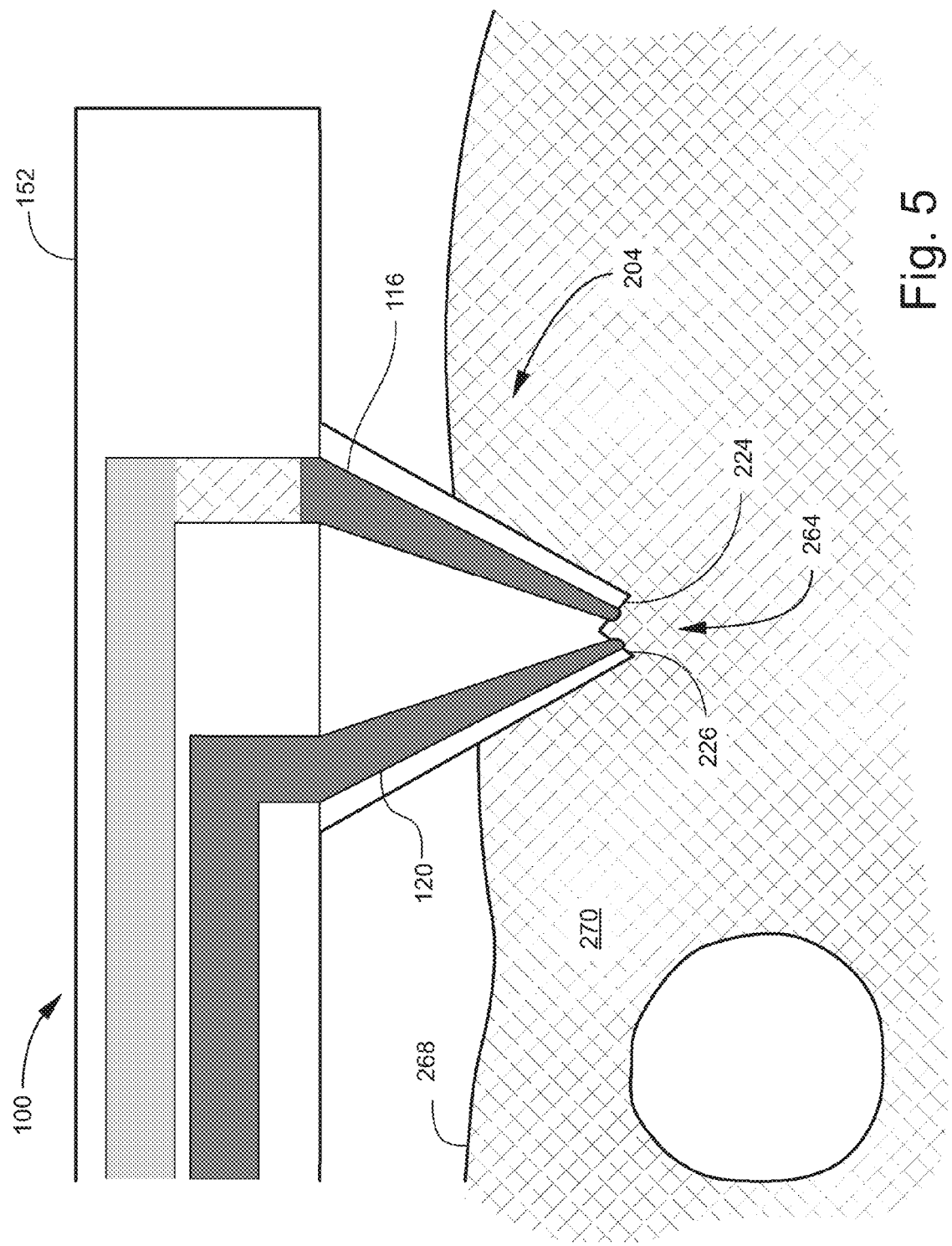
FIG. 5 is a cross-sectional side view of the sample probe illustrated in FIG. 2, wherein the sample probe is operated to aspirate the sample plug and isolator fluid according to the method, completing the isolation of the collected sample.

Referring to FIG. 5, once a sufficient volume of isolator fluid has been aspirated into the first microchannel 116 the fluids in both microchannels 116 and 120 may be withdrawn back into the probe tip 204, such as by continuing the operation of the first pump 144 and reversing the operation of the second pump 148 shown in FIG. 1. If desired, additional sample plugs may be aspirated from the same cell (not shown) by repeating the steps described above in conjunction with FIGS. 3 and 4. In this manner, each sample plug may be isolated from an adjacent sample plug by an intervening plug of isolator fluid, and all plugs may be aspirated to a downstream location together. The isolator fluid may also function to rinse the openings 224 and 226 and the walls of the microchannels 116 and 120 to prevent cross-contamination among different samples.

Figure 6:
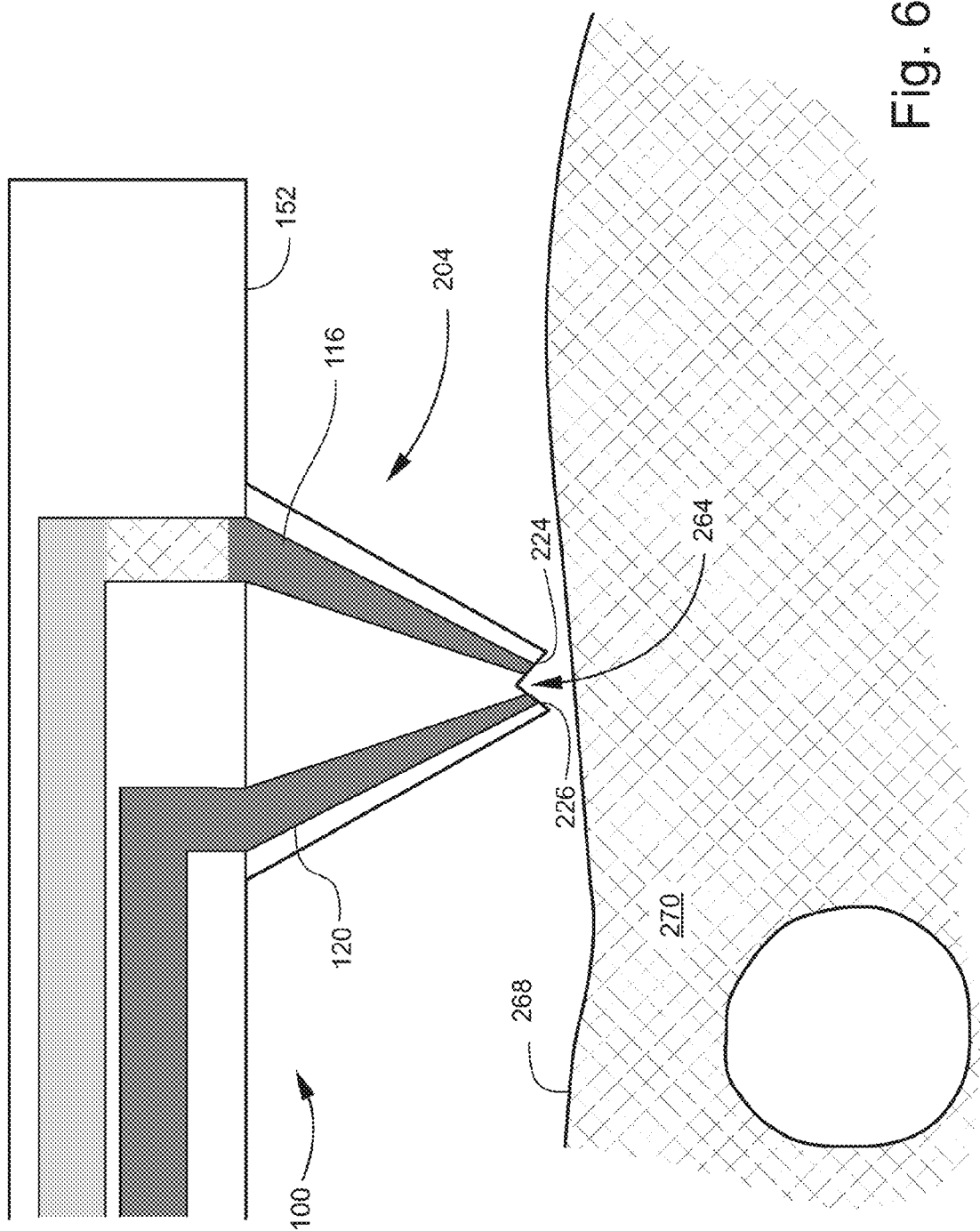
FIG. 6 is a cross-sectional side view of the sample probe illustrated in FIG. 2, wherein the sample probe is removed from the cell according to the method.

Referring to FIG. 6, after acquiring one or more sample plugs 472 from the cell 270, the probe tip 204 is withdrawn from the cell 270. At this time, flow through the microchannels 116 and 120 may be ceased and the plugs stored (held) in the microchannels 116 and 120 in the probe tip 204 and/or body 152.

Figure 7:
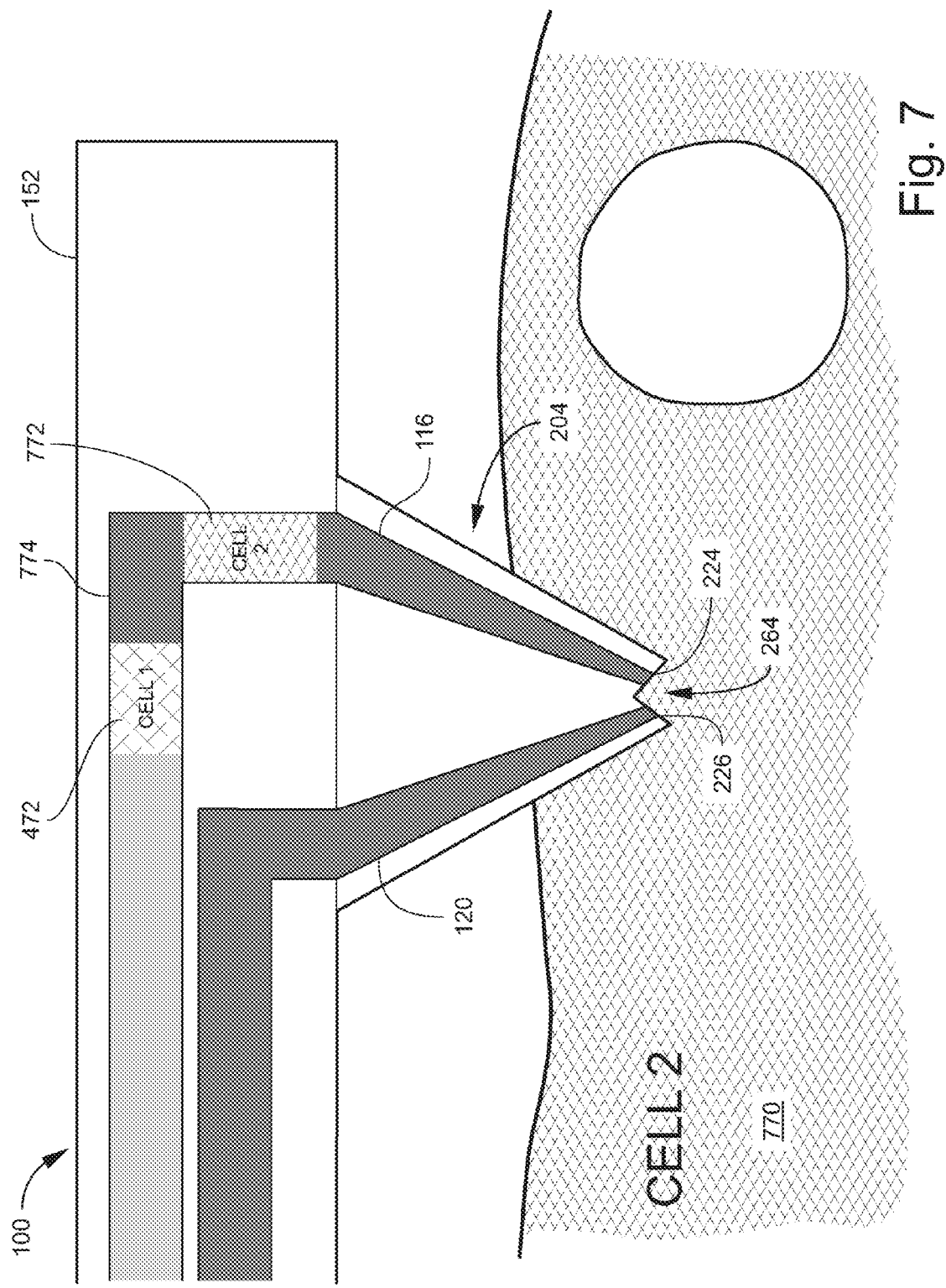
FIG. 7 is a cross-sectional side view of the sample probe illustrated in FIG. 2, wherein the sample probe is operated to aspirate intracellular material from a second cell according to the method, wherein two plugs of the contents of two or more distinct cells are isolated within a microchannel.

Referring to FIG. 7, the sample probe 100 may be moved to a second cell 770 and the probe tip 204 inserted into the second cell 770. The process described above may be repeated to aspirate intracellular fluid from the second cell 770, whereby a second sample plug 772 is formed in the first microchannel 116 and isolated from the first sample plug 472 by an intervening plug of isolator fluid (or isolator plug) 774.

The process described above in conjunction with FIGS. 2-7 may be repeated any number of times to acquire multiple sample plugs from multiple cells, with each sample plug being isolated from other sample plugs by intervening plugs of isolator fluid. The process may be repeated for as many times as desired, or to acquire as many sample plugs as may be accommodated by the sample probe 100 or by an associated fluidic system with which the sample probe 100 communicates. As shown in FIG. 7, an alternating series of plugs of intracellular fluid and plugs of isolator fluid (sample plugs 472, 772 and isolator plugs 774) may be formed in any given microchannel of the sample probe 100. This approach may be useful in applications where it is desired to maintain the order of the sample plugs acquired, such as when tracking which sample plug was extracted from which cell. In this way, the sample plugs may be correlated with the originating cells by means of cell images or their positions, and the data may be recorded by independent means. A given microchannel may have a length great enough to accommodate a desired number of sample plugs, and a characteristic dimension small enough that the sample plugs remain isolated (i.e., the sample plugs maintain contact with the walls of the microchannel and retain their shape, and contact adjacent plugs of isolator fluid only at cross-sectional interfaces). Depending on how many sample plugs are to be accommodated, the microchannel may include one or more changes in direction (e.g., may be serpentine) to maximize its length on a given surface area.

Figure 8:
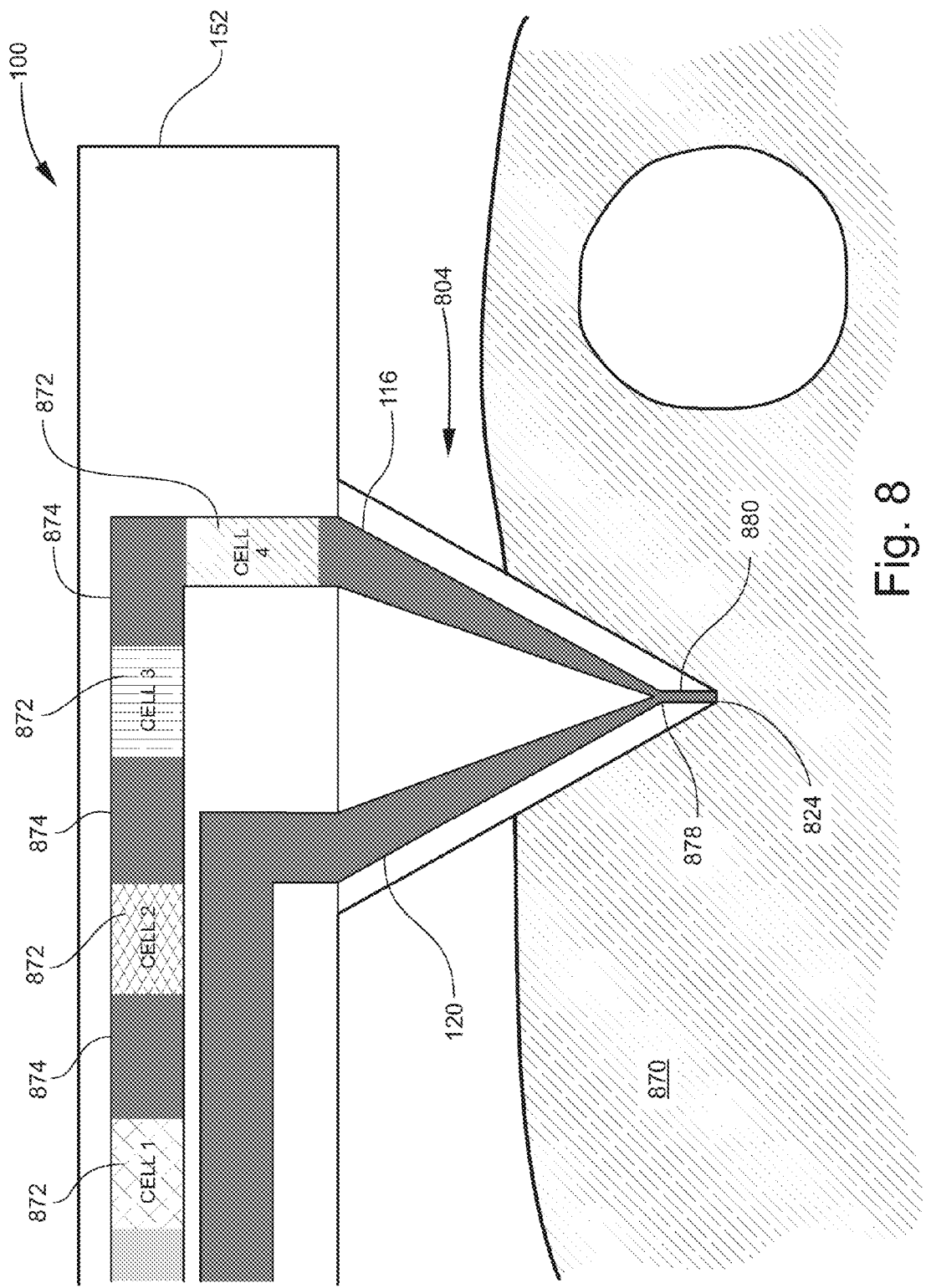
FIG. 8 is a cross-sectional side view of an example of a sample probe according to another embodiment where the probe tip has a third microchannel or cavity that intersects with the first two microchannels near the end of the probe tip, also showing the sequential storage of samples extracted from four distinct cells.

FIG. 8 is a cross-sectional side view of the sample probe 100 that includes an example of a probe tip 804 according to another embodiment. In this embodiment, two or more microchannels terminate at a common junction 878 within the probe tip 804, and the opening of the probe tip 804 is a single opening 824 communicating with the common junction 878. In the example specifically illustrated, the first microchannel 116 and second microchannel 120 terminate at the common junction 878, which is located at some distance from the opening 824. A common (or third) microchannel 880 interconnects the common junction 878 and the opening 824. With this geometry the isolation fluid may be contained entirely within the probe tip 804 during aspiration and injection operations. This geometry may be beneficial if Brownian motion or currents within a cell 870 make the diffusion of isolation fluid within the cell 870 difficult to control. In this embodiment, aspiration of intracellular material from the cell 870 into the first microchannel 116 is performed as described above. The isolator fluid in the second microchannel 120 prevents intracellular material from being aspirated into the second microchannel 120. The isolator fluid may then be pumped such that it flows through the common junction 878 and into the first microchannel 116 behind a desired volume of aspirated intracellular material, thereby forming a first sample plug. In some cases, it may be beneficial to encase the probe tip 804 and the Petri dish (or other type of sample support) in a pressurized chamber to increase the pressure available for aspiration of fluid. As described above, the process may be repeated to acquire a series of sample plugs 872 from different cells isolated by intervening isolator plugs 874.

After withdrawing the probe tip 804 from a cell and prior to inserting it into the next cell, a small amount of isolator fluid may be ejected through the opening 824 to rinse the opening 824 and common microchannel 880 between samples to minimize carryover from one sample to the next.

It will be understood that the configurations of the probe tips 204 and 804 illustrated in FIGS. 2 and 8 are merely examples. Other configurations of the microchannels, distal end, and opening(s) of a probe tip may be suitable for acquiring and isolating multiple sample plugs in accordance with the present disclosure.

Figure 9:
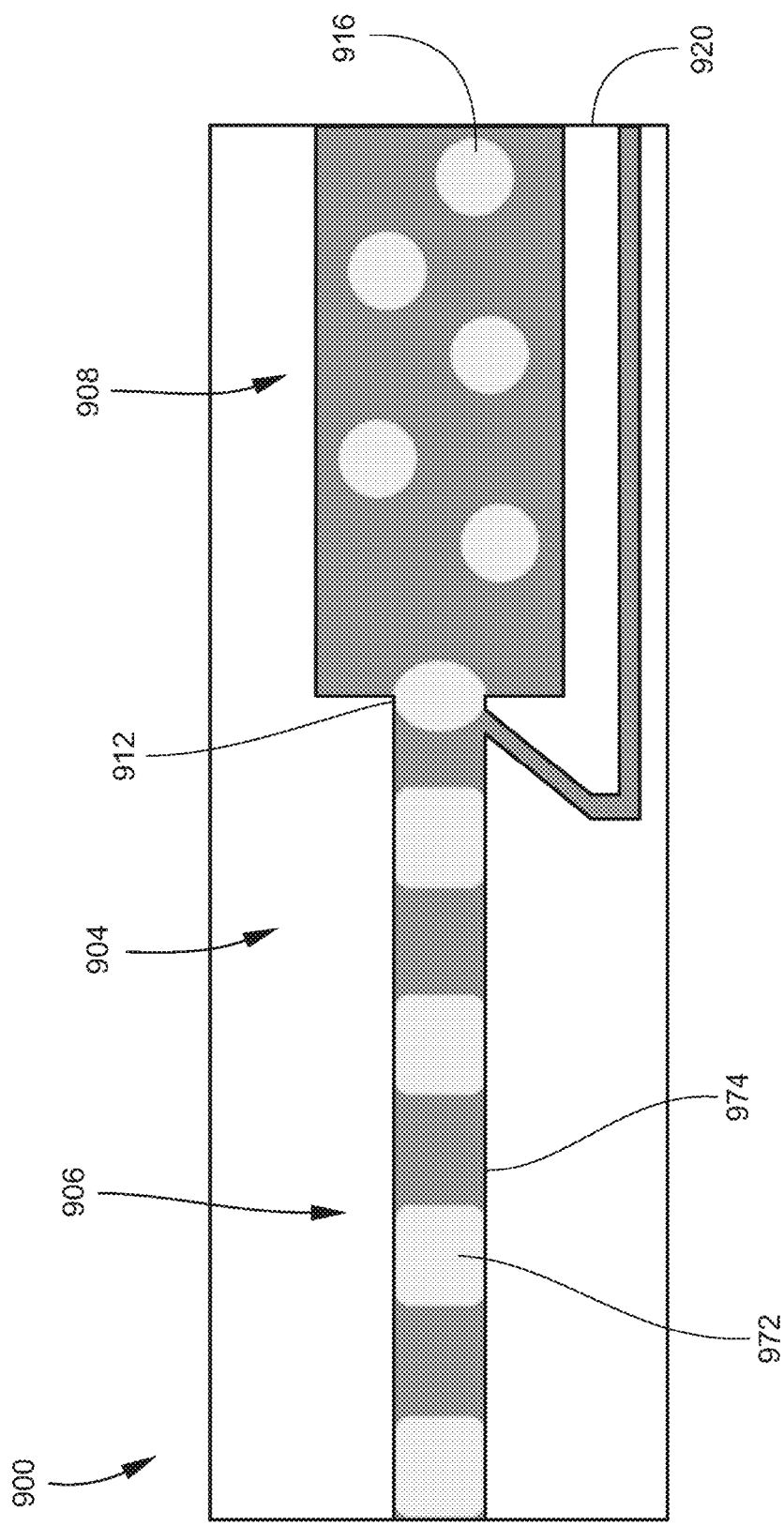
FIG. 9 is a cross-sectional view of an example of a region downstream of the tip of the sample probe according to another embodiment.

FIG. 9 is a cross-sectional view of an example of a region 900 of the sample probe 100 according to another embodiment. The region 900 may be part of the body 152 (FIG. 1), the probe tip 104, or both. The region 900 includes a microchannel 904 that may be part of or communicate with one of the tip microchannels 116, 120 or body microchannels 156, 160 shown in FIG. 1. The microchannel 904 includes a first section 906 communicating with a second section 908 at a junction or transition 912. The first section 906 may interconnect (provide fluid communication between) the second section 908 and the opening 124 of the probe tip 104 (FIG. 1), and the second section 908 may communicate with a reservoir or other downstream component. The second section 908 has at least one characteristic dimension (e.g., diameter, major axis, width, or height) that is greater than the corresponding characteristic dimension of the first section 906, such that the flow area defined by the first section 906 transitions to a larger flow area defined by the second section 908. The transition may be abrupt or somewhat abrupt as in the illustrated example, or may be more gradual over some distance. The two sections 906 and 908 may alternatively be considered as being a microchannel (the first section 906) followed by a chamber (the second section 908), respectively. The first section 906 may be narrow enough to maintain an alternating series of sample plugs 972 and isolator plugs 974 as described above, while the second section 908 may be too large to maintain the alternating series.

The region 900, illustrated in FIG. 9 may be utilized, for example, to encapsulate intracellular material into droplets 916 within an immiscible isolator fluid. Encapsulation may be useful in applications where the ordering of the sample plugs 972 is not important to interpretation of results, and randomization of the samples is acceptable. Encapsulation may be desired because a large number of droplets 916 may be stored in a second section 908 of modestly larger dimensions than the first section 906. As an example of operation, the second section 908 may be prefilled with isolator fluid, which may be the same isolator fluid utilized to isolate the sample plugs 972. The walls of the second section 908 are thus wetted by the isolator fluid. This wetting may be related to the properties of the walls such as, for example, hydrophobicity, hydrophilicity, or lipophilicity. For instance, the walls may be more hydrophobic than hydrophilic, which may enhance droplet formation. The alternating series of plugs 972, 974 is aspirated through the first section 906 and into the second section 908. In the second section 908, the sample plugs 972 are no longer restricted by the narrower characteristic dimension of the first section 906. The sample plugs 972, however, still have sufficient surface tension and immiscibility with the isolator fluid such that they are formed into droplets 916 of intracellular material in the second section 908. The droplets 916 may be accumulated and stored in the second section 908 for a desired period of time, and thereafter flowed to a downstream site.

In some applications, it may be desirable to add more of the isolation fluid by injecting it at (i.e., at or near) the junction 912, such as to assist in the formation of the droplets 916 or adjust the ratiometric volumes of the fluids. Accordingly, in some embodiments the region 900 includes a second microchannel 920 communicating with the first microchannel 904 at or near the junction 912 between the first section 906 and the second section 908. The sample probe 100 may include or communicate with a reservoir configured for supplying fluid to the first microchannel 904 via the second microchannel 920.

Figure 10:
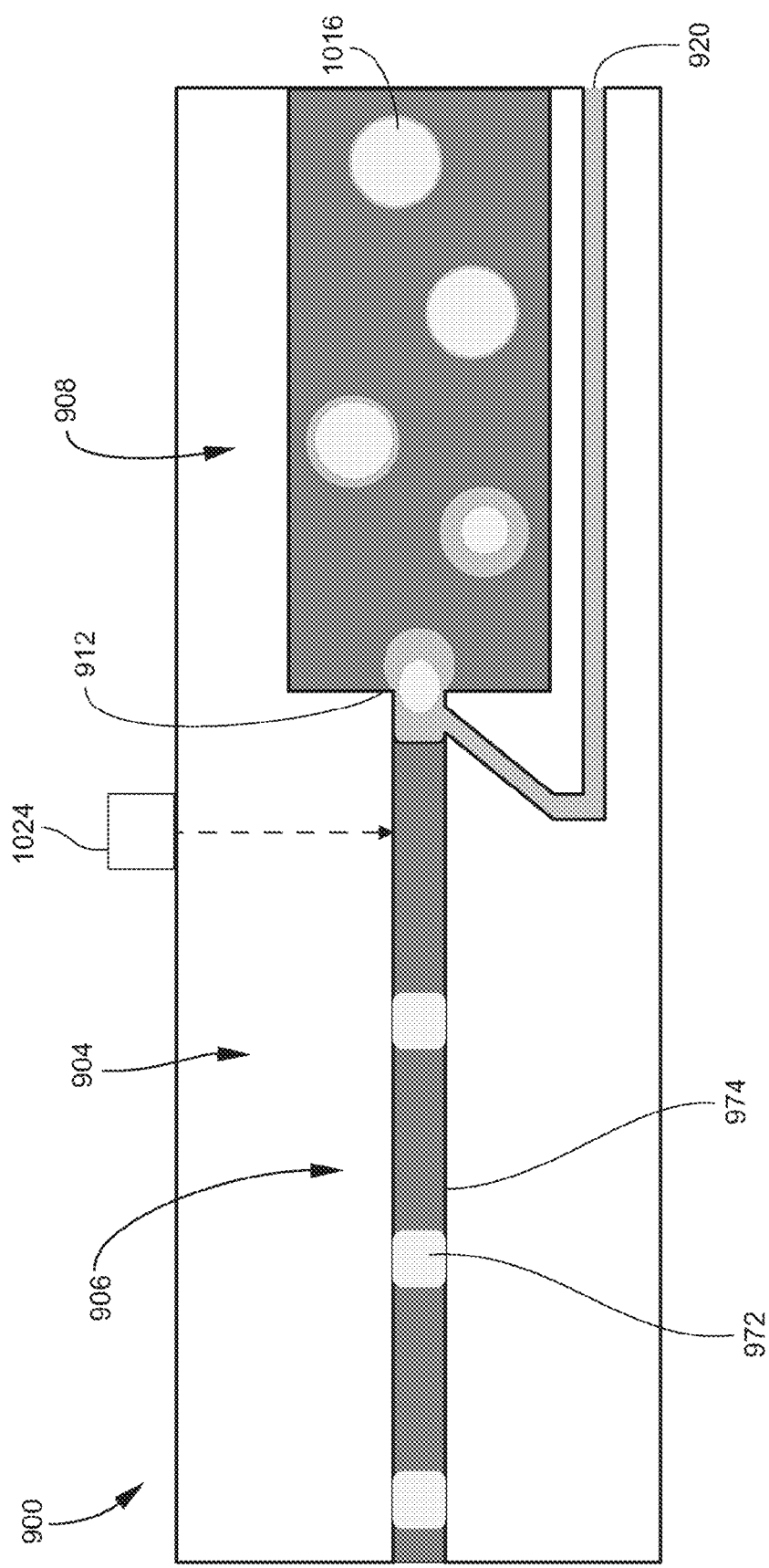
FIG. 10 is a cross-sectional view of the region illustrated in FIG. 9, wherein the region includes a sensor and additional fluid is injected to the sample plugs instead of the isolator fluid.

Referring to FIG. 10, in some applications it may be desirable to add a buffer solution to the intracellular material to change its properties (e.g., viscosity, pH), add a preservative or labeling agent, dilute the concentration of one or more of its components, or change its volume relative to the isolation fluid. The buffer solution may be an aqueous solution such as, for example, phosphate buffered saline. FIG. 10 depicts a buffer solution being added to a sample plug 1072 at the junction 912 via the second microchannel 920, and the buffer solution being dispersed in as-formed droplets 1016 in the second section 908 of the first microchannel 904.

In other embodiments, the region 900 may include one or more additional microfluidic channels that communicate with the first microchannel 904 at the first section 906 or second section 908, such as a third microchannel (not shown). One microchannel may be utilized to supply isolator fluid, another microchannel may be utilized to supply buffer solution, and additional microchannels may be utilized to supply other fluids. Each microchannel may supplied by a respective reservoir. The addition of the isolator fluid, buffer solution, or other type of fluid may make manipulation of the droplets more manageable, for example by making the properties of the intracellular material more compatible with the properties of the microfluidic surfaces.

To determine the best timing for the injection of fluids, in some embodiments the sample probe 100 may include one or more sensors 1024 of appropriate design as schematically depicted in FIG. 10. The sensor 1024 may be incorporated into the sample probe 100 or may interrogate the sample probe 100 from an external perspective. The sensor 1024 may have any configuration capable of discriminating between different types of fluids (e.g., intracellular material versus isolator fluid) flowing past the point of interrogation. As examples, the sensor 1024 may be an optical sensor that senses differences in an optical characteristic of fluids (e.g., attenuation in signal intensity, shift in wavelength, etc.), or an electrical sensor that senses differences in electrical properties of fluids (e.g., conductivities, capacitances, etc.). The sensor 1024 may be utilized to interrogate a location such as shown in FIG. 10 to ensure that the correct fluid is injected into the correct plug of fluid at the most appropriate time. For example, the sensor 1024 may detect each sample plug 1072 as it approaches the junction 912, and then produce an output signal utilized to cause a pump to inject buffer solution into the sample plug 1072 as it enters the second section 908.

Figure 11:
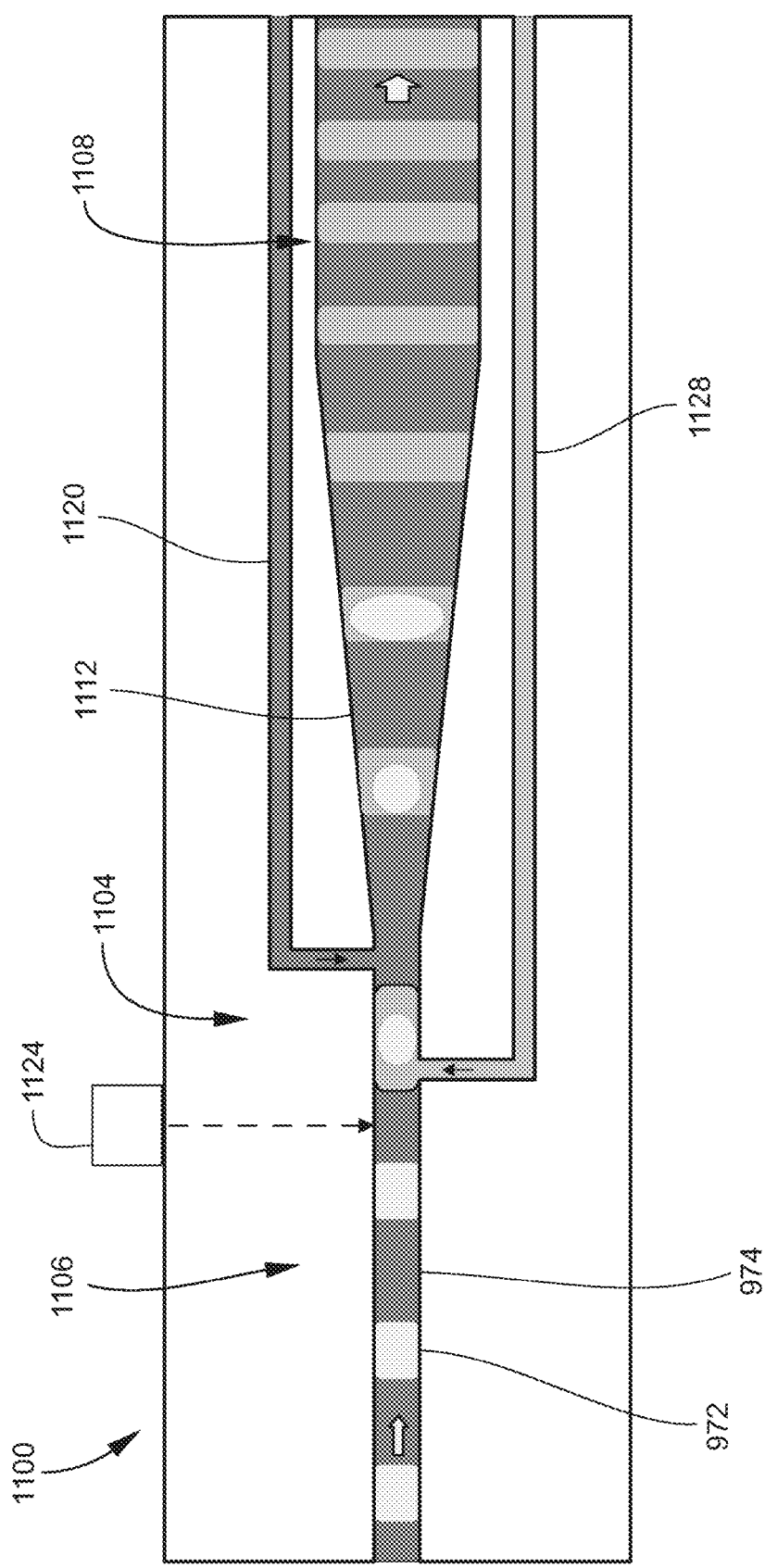
FIG. 11 is a cross-sectional view of an example of a region of the sample probe downstream of the tip according to another embodiment wherein an additional fluid is added and the width of the channel is subsequently increased to reduce the resistance to flow.

FIG. 11 is a cross-sectional view of an example of a region 1100 of the sample probe 100 according to another embodiment. The region 1100 may be part of the body 152 (FIG. 1), the probe tip 104, or both. The region 1100 includes a first microchannel 1104 that may be part of or communicate with one of the tip microchannels 116, 120 or body microchannels 156, 160 shown in FIG. 1. The first microchannel 1104 includes a first section 1106 communicating with a second section 1108 at a junction or transition 1112. The first section 1106 may interconnect the second section 1108 and the opening 124 of the probe tip 104 (FIG. 1), and the second section 1108 may communicate with a reservoir or other downstream component. The second section 1108 has at least one characteristic dimension that is greater than the corresponding characteristic dimension of the first section 1106, such that the flow area defined by the first section 1106 transitions to a larger flow area defined by the second section 1108. In the present embodiment, the junction 1112 is a length of microchannel that is tapered (specifically, diverging in the direction toward the second section) 1108 such that transition is gradual. The two sections 1106 and 1108 may alternatively be considered as being a microchannel (the first section 1106) followed by a chamber (the second section 1108), respectively. The larger second section 1108 may be desirable for various reasons, such as providing a transition from the smaller first section 1106 to a larger downstream microfluidic element, or reducing flow resistance or back pressure in the first microchannel 1104. However, while the first section 1106 may be narrow enough maintain an alternating series of sample plugs 1172 and isolator plugs 1174, the second section 1108 may be too large to maintain the alternating series unless some manipulation of the fluids is performed. If either a sample plug 1172 or an isolator plug 1174 becomes too small in the direction of travel, then that plug may form a droplet within an adjacent plug.

In the illustrated embodiment, the region 1100 includes a second microchannel 1120 and a third microchannel 1128 communicating with the first microchannel 1104 at the first section 1106, the junction 1112, or the second section 1108. For example, the second microchannel 1120 may be utilized to add isolator fluid to isolator plugs 1174 and third microchannel 1128 may be utilized to add buffer solution to sample plugs 1172. As described above, one or more sensors 1124 may be provided to identify the type of plug 1172 or 1174 passing a selected point of interrogation and activate the appropriate microchannel 1128 or 1120. The fluids added by the microchannels 1120 and 1128 may function to maintain continuous, stable plugs that span transversely from wall to wall across the microchannel 1104, even as the microchannel 1104 increases in cross-section, thereby keeping successive sample plugs isolated from each other. Either or both microchannels 1120, 1128 may be activated for this purpose, depending on the application. The hydrophobic/hydrophilic properties of the channel walls may play a role in maintaining the stability of fluid plugs and may affect their dynamics within the microchannel 1104. These properties may be tuned and controlled through the use of appropriate surface chemistries, as appreciated by persons skilled in the art.

Figure 12:
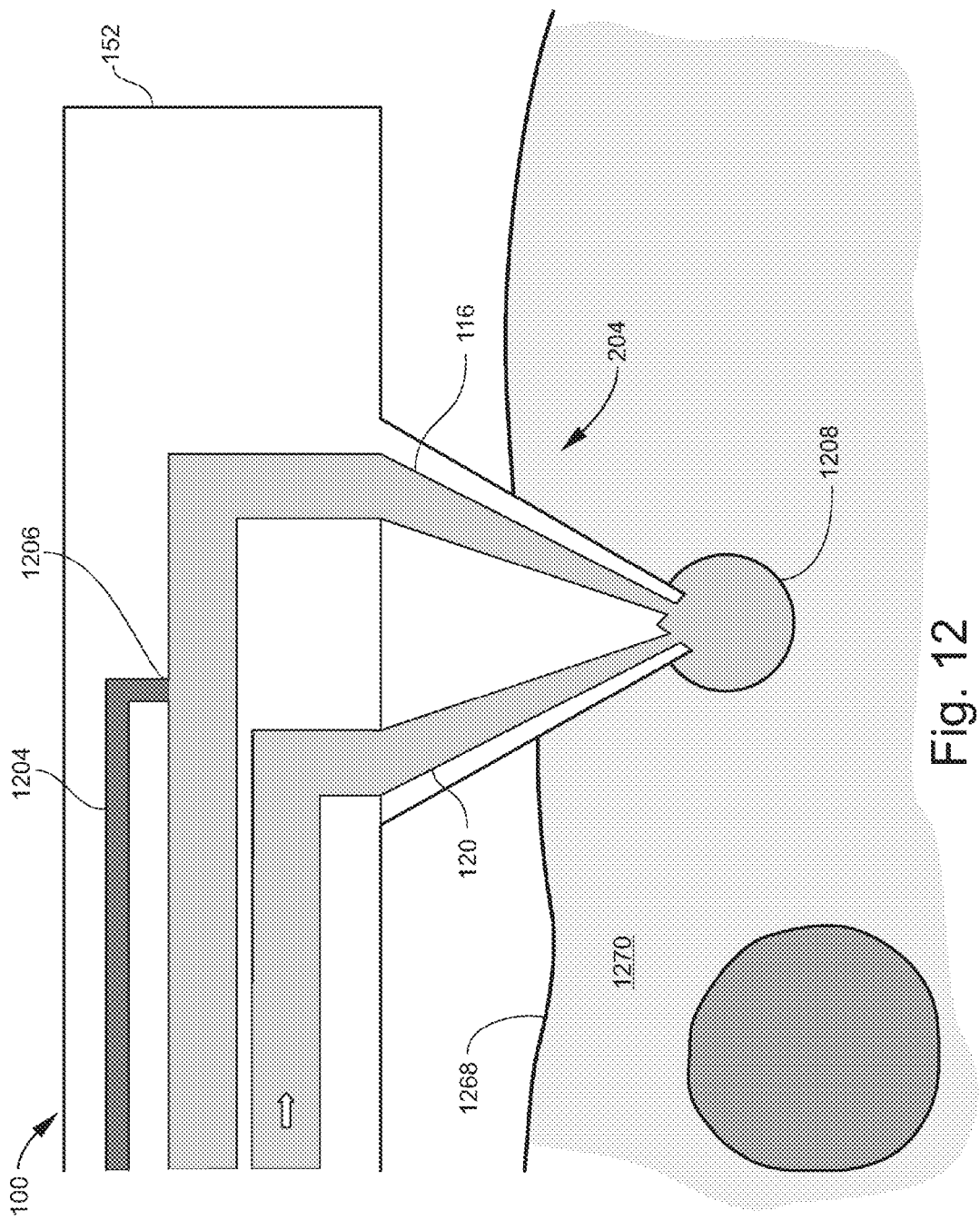
FIG. 12 is a cross-sectional side view of an example of a sample probe according to another embodiment.

Another example of a method for sampling intracellular material will now be described with reference to FIGS. 12-16. Referring to FIG. 12, in this embodiment the first microchannel 116 may be utilized as an output channel for aspirating sample plugs, and the second microchannel 120 may be utilized as an input channel for injecting buffer solution. In addition, in this embodiment the sample probe 100 may include a third microchannel (or isolator fluid supply microchannel) 1204 communicating with the first microchannel 116 at a junction 1206 for adding isolator fluid to the first microchannel 116. The junction 1206 may be located in the body 152 of the sample probe 100 as shown, or alternatively in the probe tip 204.

Figure 13:
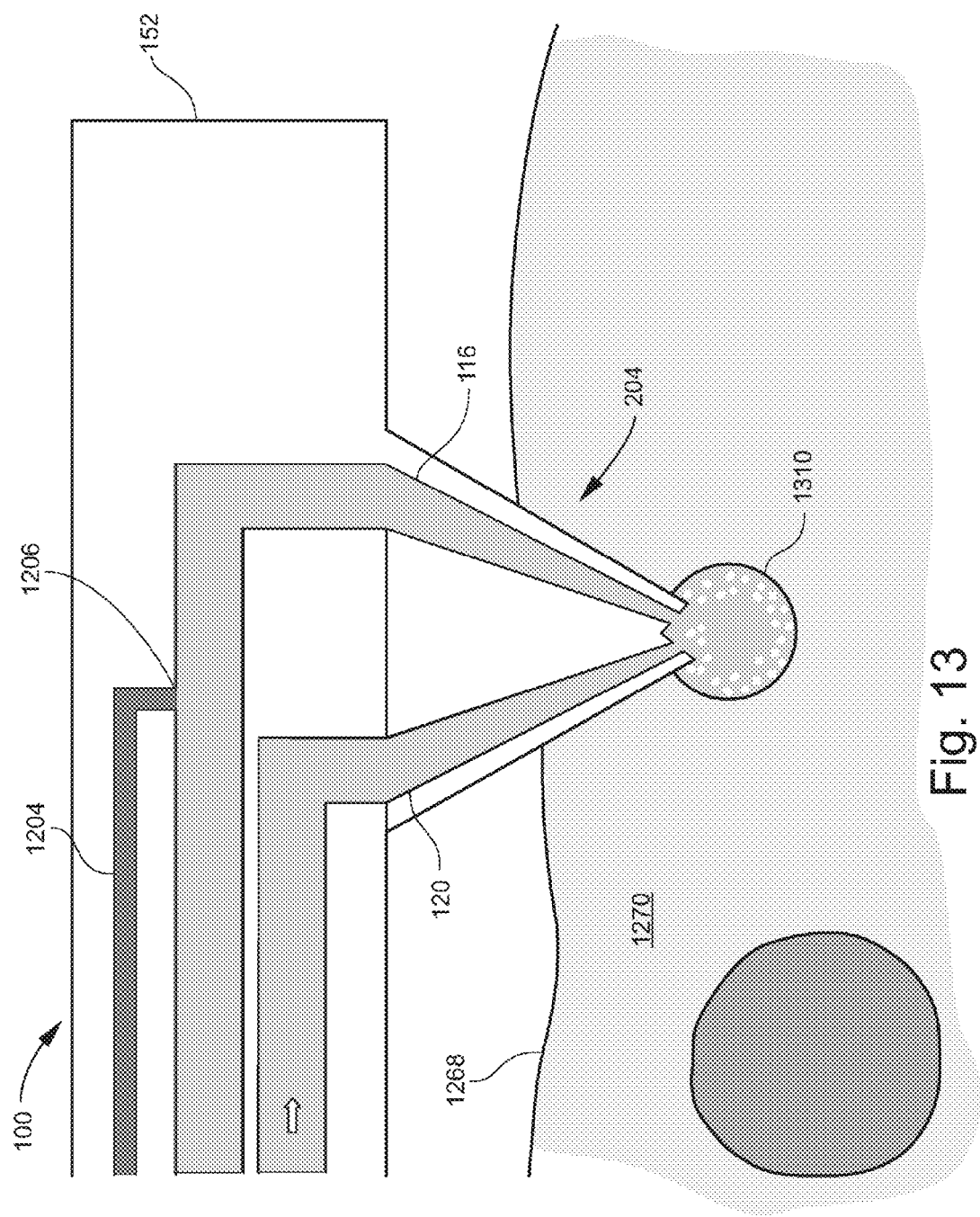
FIG. 13 is a cross-sectional side view of the sample probe illustrated in FIG. 12, wherein the sample probe is operated to inject a buffer solution into a cell whereby intracellular material diffuses into the buffer solution, according to an example of another method disclosed herein.
Figure 14:
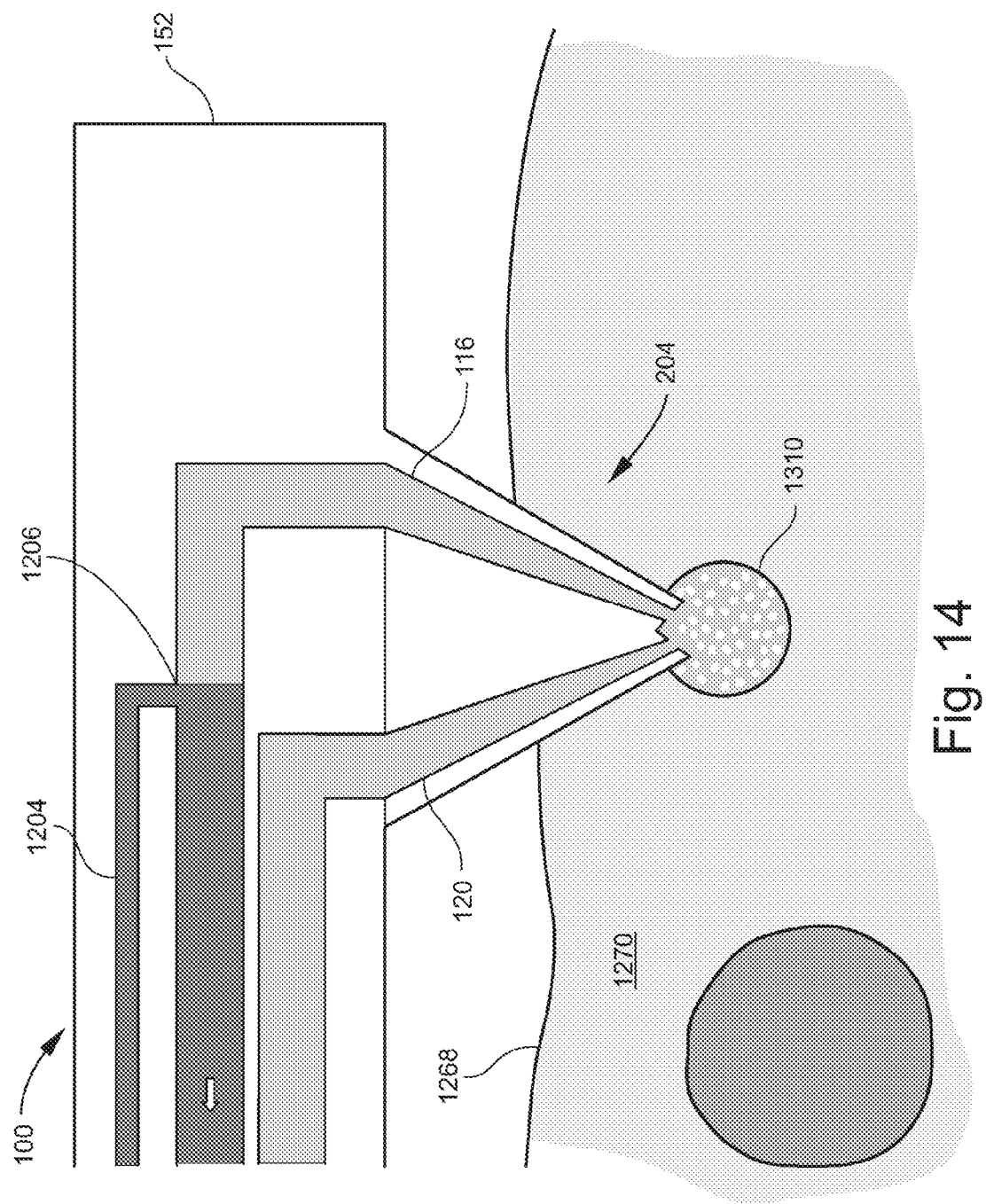
FIG. 14 is a cross-sectional side view of the sample probe illustrated in FIG. 12, wherein the sample probe is operated to establish a flow of isolator fluid in the sample probe according to the method.
Figure 15:
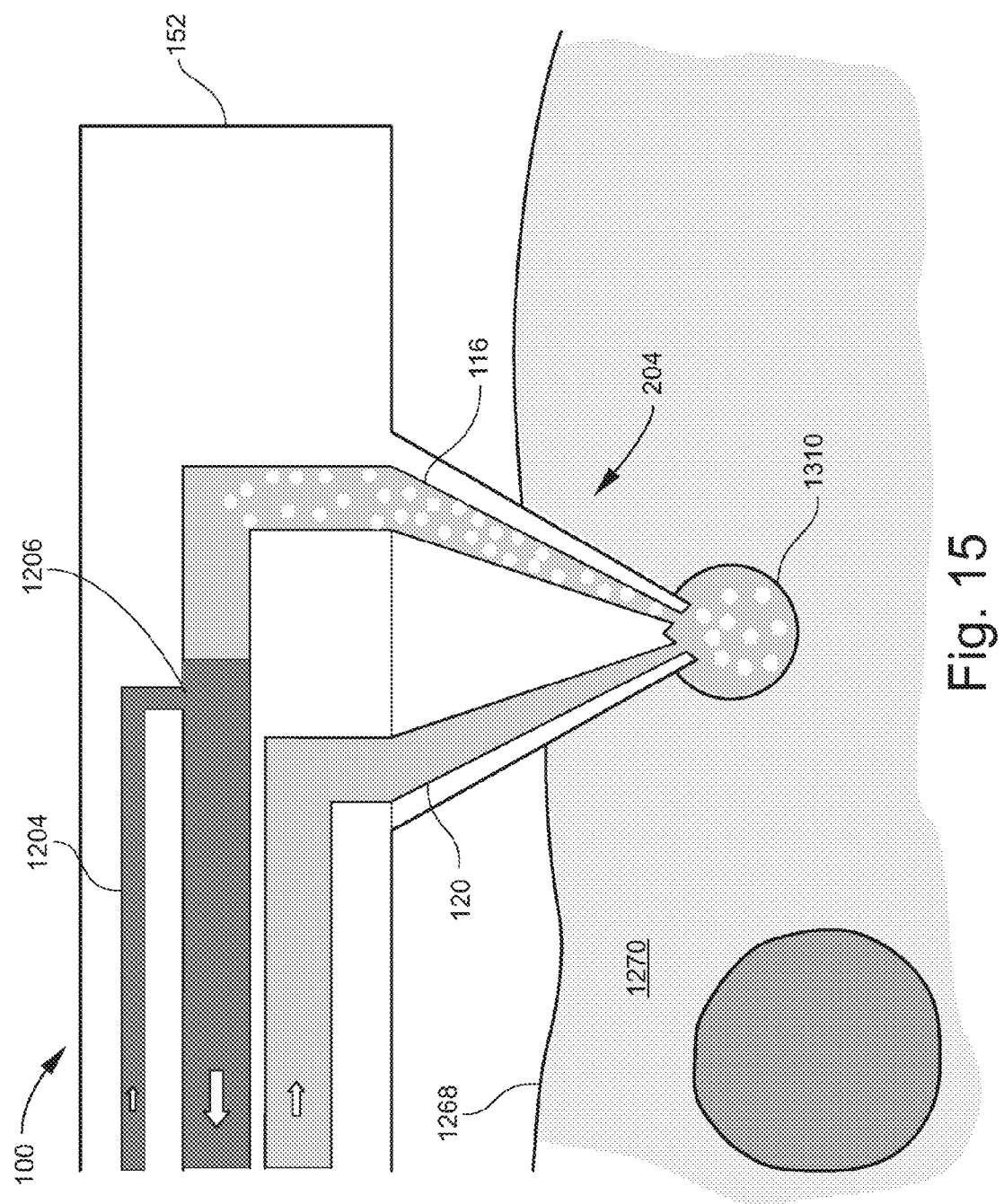
FIG. 15 is a cross-sectional side view of the sample probe illustrated in FIG. 12, wherein the sample probe is operated to aspirate a mixture of the buffer solution and intracellular material from the cell.
Figure 16:
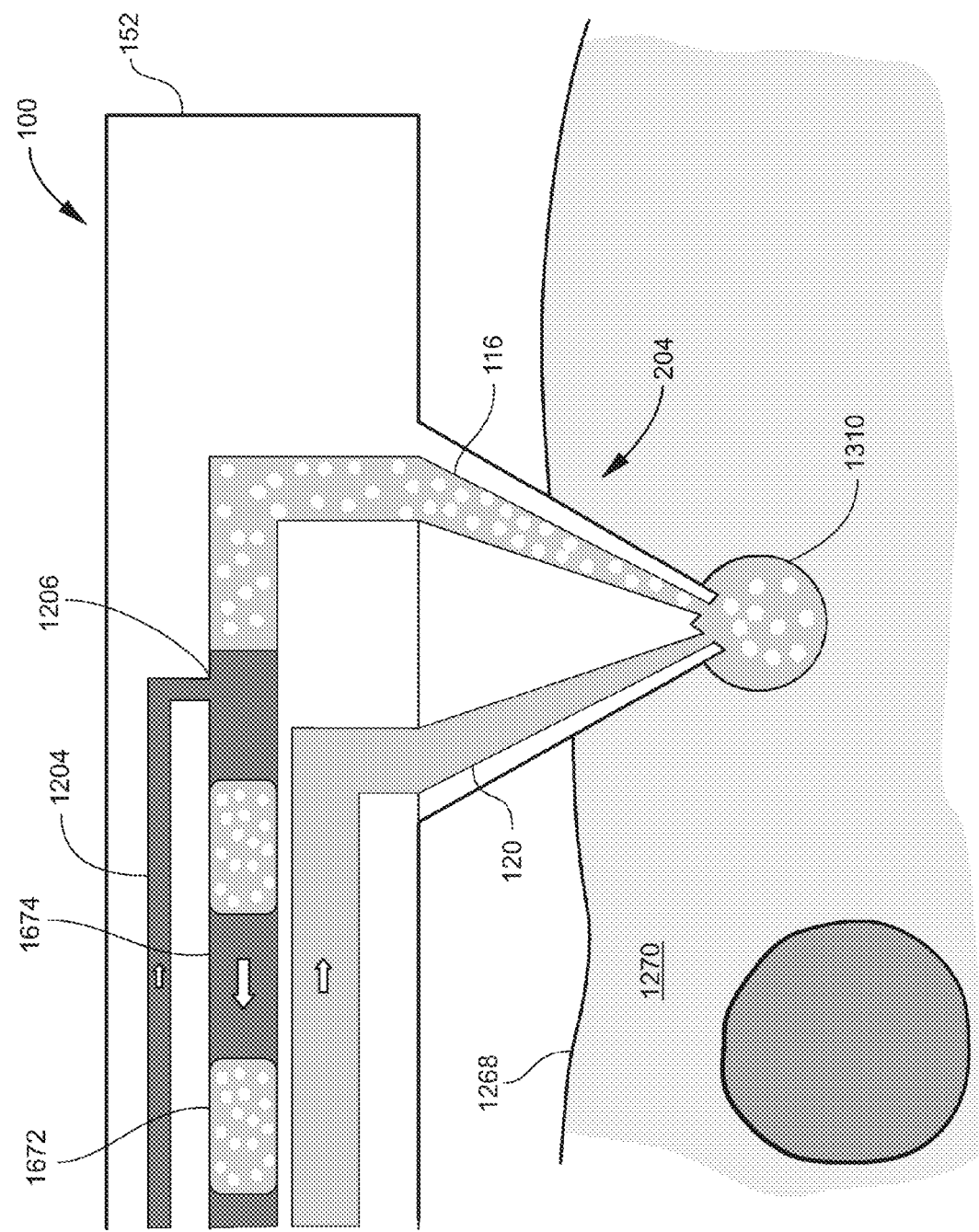
FIG. 16 is a cross-sectional side view of the sample probe illustrated in FIG. 12, wherein the sample probe is operated to form alternating plugs of the mixture and isolator fluid.

Referring to FIG. 12, the sample probe 100 is moved to a selected cell 1270 and lowered toward the cell 1270 until the distal end of the probe tip has penetrated a membrane 1268 of the cell 1270. A small amount of buffer solution is injected into the cell interior from the second microchannel 120. In the present context, the buffer solution may be any fluid that is readily miscible with the intracellular material to be aspirated. The injected buffer solution briefly forms a droplet 1208 into which intracellular material can diffuse. Referring to FIG. 13, a small fraction of intracellular material diffuses into the injected buffer solution, forming a zone or region 1310 of combined (mixed) fluid in the cell interior or, stated another way, a zone or region 1310 of intracellular material that is enriched with buffer solution. This diffusion may occur rapidly. Referring to FIG. 14, prior to or while beginning to aspirate the mixed fluid in the zone 1310, a flow of immiscible isolator fluid is established from the third microchannel 1204 into the first microchannel 116 in the output direction. Referring to FIG. 15, quickly after the zone 1310 is formed the mixed fluid in the zone is aspirated into the first microchannel 116. Referring to FIG. 16, as the mixed fluid continues to be aspirated the isolator fluid is intermittently pumped into the first microchannel 116, thereby forming an alternating series of sample plugs 1672 (containing the mixed fluid) and isolator plugs 1674 in the first microchannel 116. The sample plugs 1672 may be transported to and processed at downstream sites, and the process may be repeated for one or more additional cells, as described elsewhere in this disclosure. The timing of the fluid flows and the volumes of fluids involved in this method may be optimized as needed to achieve the appropriate ratio of cell contents and buffer solutions as well as the appropriate plug sizes.

As cells are dense with proteins and other biological molecules, the viscosity of the aspirated mixed fluid is typically about an order of magnitude lower than the cellular contents itself, and also less variable and easier to control. Also, the cellular volumes are already quite small, and the volumes of the intracellular material to be extracted are a small fraction of the cellular volume. The method described above in conjunction with FIGS. 12-16 allows an expansion of the volume of fluid making it easier to control and isolate. This means that larger channel cross-sections may be enabled, reducing the resistance to flow of fluid through the microchannels. This, combined with the much lower viscosity of the extracted mixed fluid, means that the pressures that must be applied to move the fluids into and out of the cell as well as pump them through the microchannels is much lower than would be the case for undiluted cytoplasm or nuclear media. Another advantage is that the immiscible isolator fluid may be kept away from the end of the probe tip 204, reducing the level of contamination of the immiscible fluid into the cell. The isolator fluid may be introduced at a point farther away from the probe tip 204 than the junction 1206 shown by example in FIGS. 12-16.

In another embodiment, the sample probe 100 including the probe tip 804 illustrated in FIG. 8 may include the third microchannel 1204 and may be utilized to implement the method described above and illustrated in FIGS. 12-16.

In another embodiment, the sample probe 100 including the third microchannel 1204 illustrated in FIGS. 12-16 may be utilized to implement the method described above and illustrated in FIGS. 2-7. In this case, the second microchannel 120 may be utilized to inject fluids other than the isolator fluid, or to aspirate fluids from the cell, or may not be utilized.

Figure 17:
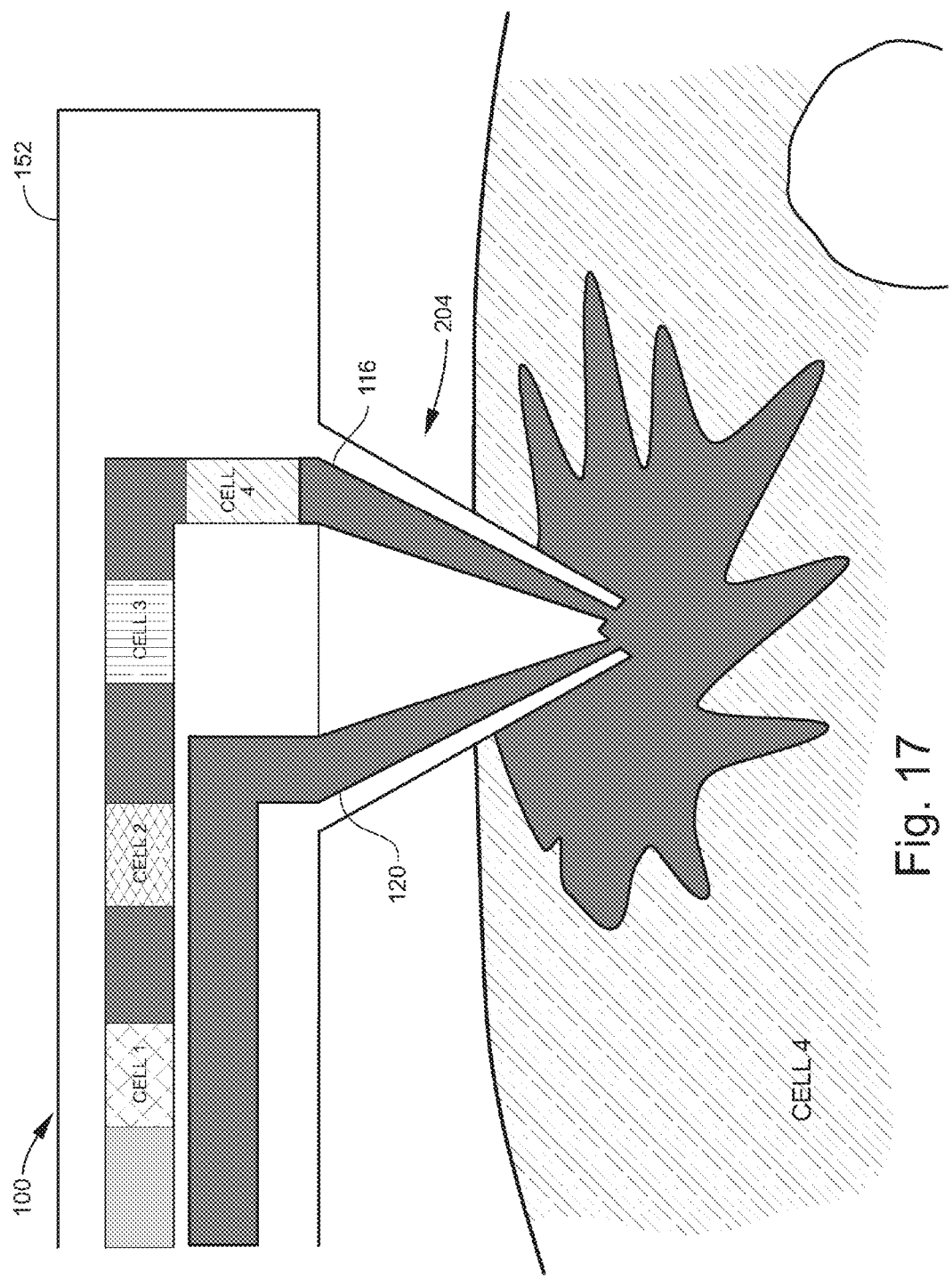
FIG. 17 is a cross-sectional side view of the sample probe illustrated in FIG. 2, wherein the sample probe is operated to inject a labeling agent into a cell.

In other embodiments, any of the sample probes illustrated in FIGS. 2-7, FIG. 8, and FIGS. 12-16, respectively, may be utilized to label cells during the aspiration procedure. For example, in the sample probe 100 of FIGS. 2-7 the isolation fluid may include a labeling agent (e.g., dye, fluorescent molecules, etc.) and once the sample plug is isolated from the cell, some of the labeling agent may be either directly injected into the cell or left as a byproduct of the extraction procedure. This example is depicted in FIG. 17. Labeling agent-inclusive isolator fluid may be injected in a similar manner by the sample probe 100 of FIG. 8. In the sample probe 100 of FIGS. 12-16, the buffer solution may contain a labeling agent that may diffuse into the cell during the sampling process. In some applications, the ability to use a fluid that mixes readily with cellular contents may provide an advantage over use of an immiscible fluid for labeling cells. In other embodiments, a microchannel of the probe tip may be dedicated for injecting a labeling agent, or the sample probe may include two probe tips—one for sampling and one for delivering labeling reagents. All such embodiments may allow a user to know which cells have undergone extraction, and enable the user to monitor these cells with respect to unmarked cells to ascertain the level of damage due to the extraction of material or to allow sampling of the same cell at multiple time points to ascertain natural temporal variation or changes due to specific chemical or biological stimuli. Labeling agents may also be included to assist in distinguishing between the isolator fluid and sample material.

Figure 18:
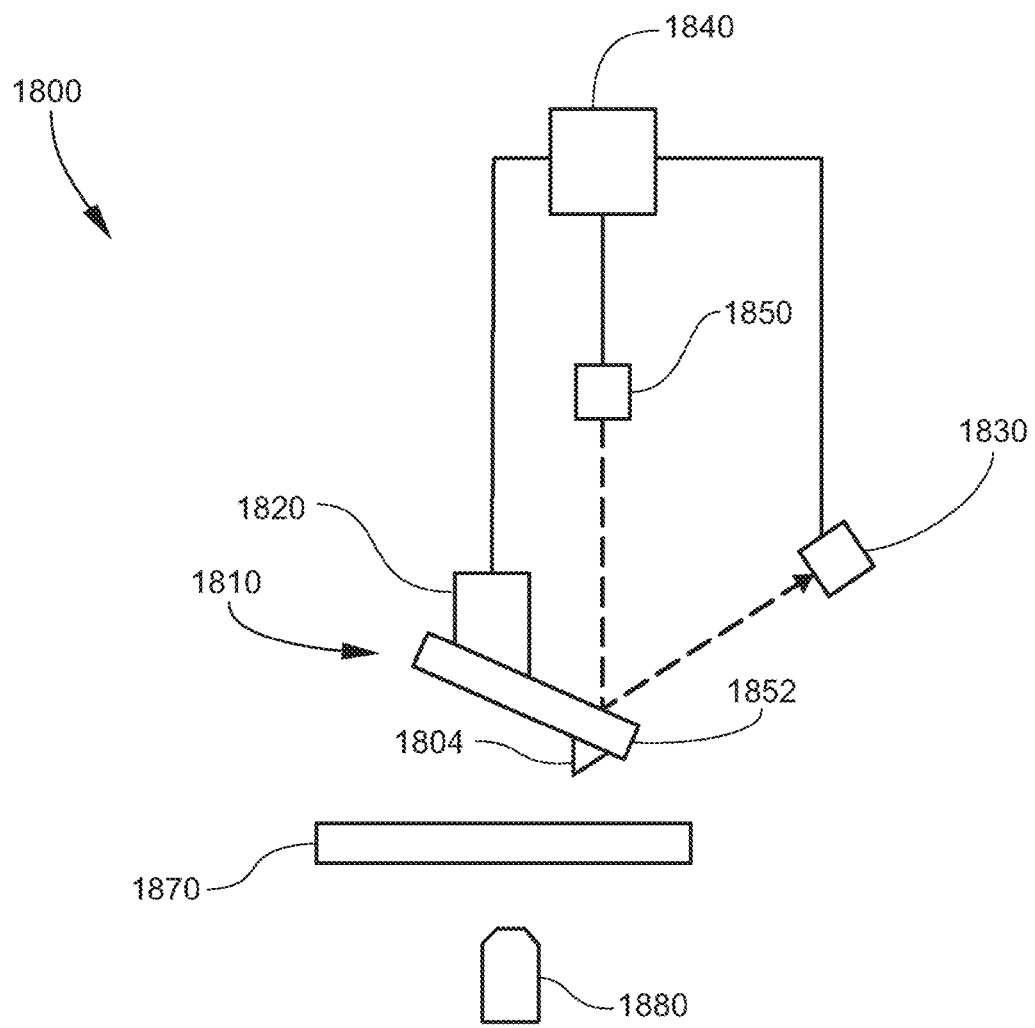
FIG. 18 is a schematic view of a system (or part of the system) in which an AFM-based sample probe may be utilized.

FIG. 18 is a schematic view of a system (or part of the system) 1800 in which an AFM-based sample probe 1810 may be utilized. The sample probe 1810 is shown positioned above a cell holder 1870 that may contain one or more cells (not shown). The sample probe 1810 includes a probe tip 1804 and deflectable body 1852 as described above. The sample probe 1810 is mounted to a staging device 1820. The staging device 1820 may be capable of three-dimensional (X-Y-Z) movement for lowering and raising the probe tip 1804 relative to a selected cell, and for translating the probe tip 1804 in a horizontal plane over a selected cell and from one cell to another. Alternatively, the cell holder 1870 may be supported by a staging device (not shown) capable of moving the cell holder 1870 in one or more dimensions. In some embodiments, the staging device may include one staging part that supports the sample probe 1810 and another staging part that supports the cell holder 1870, with one or both staging parts configured for movement in less than three dimensions. For example, the staging part supporting the sample probe 1810 may operate in one dimension for inserting the probe tip 1804 into a cell and removing the probe tip 1804 from the cell, while the staging part supporting the cell holder 1870 may operate in two dimensions for translating the cell holder 1870 in a horizontal plane relative to the probe tip 1804. The system 1800 may also include a detector 1830 configured for measuring an amount of deflection of the body 1852 and provide output signals (e.g., force feedback signals) to any suitable system controller 1840 (e.g., an electronic processor-based controller, as appreciated by persons skilled in the art). In some embodiments, the detector 1830 is an optical detector that receives a light beam (dashed arrow) produced by a light source 1850 (e.g., laser) and reflected from a surface of the body 1852. As evident from the foregoing, the system 1800 may be considered as including an atomic force microscope to which the sample probe 1810 is mounted, or of which the sample probe 1810 is a part. In addition, the system 1800 can be integrated with an inverted light microscope, as schematically depicted by an objective 1880 under the cell holder 1870. The light microscope enables optical guidance for positioning of the probe tip 1804 relative to a cell of interest. Other components and functions that may be provided by the system 1800 for AFM and optical microscopy-based operations are readily appreciated by persons skilled in the art.

The system 1800 depicted in FIG. 18 may be utilized for high-resolution (e.g., on the order of nanometers) staging and positioning of the sample probe 1810 relative to a selected cell, and precise monitoring of the probe tip 1804 during contact, indentation and penetration of the cell membrane. The system 1800 may also be utilized for conventional AFM imaging of cells or force spectroscopy measurements. The light microscope may also be utilized for various tasks related to cell imaging, such as time lapse imaging and tracking individual cells over time. As another example, the probe tip 1804 may be utilized to inject a reagent into a cell while the light microscope is utilized to monitor the cell's response to the reagent or the cell's response to being probed or aspirated.

EXEMPLARY EMBODIMENTS

Exemplary embodiments provided in accordance with the presently disclosed subject matter include, but are not limited to, the following:

1. A sample probe, comprising: a tip comprising a distal end configured for penetrating a cellular membrane, an opening located at or proximal to the distal end, and a plurality of tip microchannels extending through the tip and communicating with the opening; and a body adjoining the tip and comprising a plurality of body microchannels, wherein at least one of the body microchannels communicates with at least one of the tip microchannels.

2. The sample probe of embodiment 1, wherein the body is a deflectable cantilever suitable for atomic force microscopy.

3. The sample probe of embodiment 2, comprising a detector configured for measuring an amount of deflection of the body, and a staging device configured for moving the tip relative to a cell or the cell relative to the tip.

4. The sample probe of embodiment 1, wherein each tip microchannel has a cross-sectional dimension ranging from 0.1 nm to 1 nm.

5. The sample probe of embodiment 1, wherein the distal end has a tapered profile terminating at an apex, and the opening is located at or proximal to the apex.

6. The sample probe of embodiment 1, wherein the distal end comprises an annular apex circumscribing a cavity extending into the tip, and the opening communicates with the cavity.

7. The sample probe of embodiment 1, wherein the opening comprises a plurality of orifices, each orifice communicating with at least one of the tip microchannels.

8. The sample probe of embodiment 1, wherein one of the tip microchannels is a common microchannel interconnecting the opening with at least two other tip microchannels at a junction in the tip.

9. The sample probe of embodiment 1, wherein the plurality of tip microchannels or body microchannels comprises: a first microchannel comprising a first section and a second section, the first section interconnecting the second section with the opening and having a first characteristic dimension, and the second section having a second characteristic dimension greater than the first characteristic dimension; and a second microchannel communicating with the first microchannel at or near a junction between the first section and the second section.

10. The sample probe of embodiment 9, comprising a sensor communicating with the first microchannel and configured for producing a signal indicative of a type of fluid passing through the junction.

11. The sample probe of embodiment 1, comprising a first pump configured for transporting fluid from at least one of the tip microchannels to the opening, and a second pump configured for aspirating fluid from the opening to at least one other tip microchannel.

12. A method for sampling intracellular material, the method comprising: inserting a tip of a probe through a membrane of a cell; aspirating intracellular material from the cell, through an opening of the tip, and into a first microchannel of the tip; flowing isolator fluid from a second microchannel of the tip into the first microchannel to form a plug of intracellular material defined in part by a boundary between the intracellular material and the isolator fluid; and aspirating the plug and the isolator fluid through the first microchannel.

13. The method of embodiment 12, comprising aspirating the plug and the isolator fluid from the first microchannel to a destination selected from the group consisting of: a downstream microchannel of the probe; a port of the probe; a reservoir of the probe; a reservoir communicating with the probe; and a downstream microchannel extending through a deflectable cantilever of the probe wherein the deflectable cantilever is configured for mounting to an atomic force microscope.

14. The method of embodiment 12, comprising repeating the steps of aspirating intracellular material and flowing isolator fluid into the first microchannel one or more times to form an alternating series of plugs of intracellular material and isolator fluid.

15. The method of embodiment 12, wherein the cell is a first cell and the plug of intracellular material is a first plug, and further comprising: removing the tip from the first cell; inserting the tip into a second cell; aspirating intracellular material from the second cell, through the opening, and into the first microchannel; and flowing isolator fluid from the second microchannel into the first microchannel to form a second plug of intracellular material from the second cell.

16. The method of embodiment 15, wherein the second plug is formed before aspirating the first plug to a downstream location, such that the second plug is isolated from the first plug in the first microchannel by the isolator fluid between the first plug and the second plug, and further comprising aspirating the first plug, the second plug and the isolator fluid to the downstream location in a single aspiration step.

17. The method of embodiment 15, comprising forming an alternating series of plugs in the first microchannel, the alternating series comprising the first plug, the second plug, and one or more additional plugs of intracellular material, wherein each plug of intracellular material is isolated from an adjacent plug of intracellular material by an intervening plug of isolator fluid, and wherein forming the alternating series comprises repeating the removing, inserting, aspirating and flowing steps of claim 15 one or more times for one or more additional cells.

18. The method of embodiment 12, wherein the plug of intracellular material has a volume ranging from $10^{-13}$ liters to $10^{-15}$ liters.

19. The method of embodiment 12, wherein the isolator fluid is immiscible with the intracellular material.

20. The method of embodiment 12, wherein flowing the isolator fluid comprises: flowing the isolator fluid from the second microchannel and through the opening to form a bulb of isolator fluid that blocks further aspiration of the intracellular material from the cell into the first microchannel; and aspirating the isolator fluid through the opening and into the first microchannel.

21. The method of embodiment 20, wherein an outer surface of the tip comprises a cavity, the opening comprises a first orifice and a second orifice located at the cavity, the first orifice communicates with the first microchannel and the second orifice communicates with the second microchannel, and wherein the bulb is formed in the cavity to isolate the first orifice from an interior of the cell.

22. The method of embodiment 12, wherein the tip comprises a third microchannel communicating with the opening and interconnecting the first microchannel and the second microchannel at a junction in the tip, and wherein the isolator fluid is flowed from the second microchannel into the first microchannel via the junction such that the isolator fluid at the junction blocks further aspiration of the intracellular material from the cell into the first microchannel.

23. The method of embodiment 12, comprising: repeating the steps of aspirating intracellular material and flowing isolator fluid into the first microchannel one or more times to form an alternating series of plugs of intracellular material and isolator fluid; and flowing the alternating series of plugs from the first microchannel into a downstream microchannel having a larger cross-sectional dimension than the first microchannel.

24. The method of embodiment 23, wherein the isolator fluid is immiscible with the intracellular material, and further comprising forming the plugs of the intracellular material into respective droplets in the downstream microchannel.

25. The method of embodiment 24, comprising at least partially filling the downstream microchannel with isolator fluid prior to flowing the alternating series of plugs into the downstream microchannel.

26. The method of embodiment 23, comprising maintaining contact between the plugs of the intracellular material and a wall defining the downstream microchannel while flowing the plugs of the intracellular material through the downstream microchannel.

27. The method of embodiment 23, comprising injecting an additional fluid into the flow of the alternating series of plugs at a location at or near an inlet of the downstream microchannel through which the plugs pass, wherein the additional fluid is selected from the group consisting of the isolator fluid, a buffer fluid, and both the isolator fluid and the buffer fluid.

28. The method of embodiment 27, comprising selecting one or more of the plugs to receive the additional fluid, wherein the additional fluid is injected into the one or more selected plugs.

29. The method of embodiment 28, wherein selecting the one or more plugs comprises determining whether a plug is a plug of intracellular material or a plug of isolator fluid.

30. The method of embodiment 12, comprising injecting a quantity of the isolator fluid into the cell, and removing the tip from the cell with the quantity of the isolator fluid remaining in the cell, wherein the isolator fluid comprises a labeling agent.

31. A method for sampling intracellular material, the method comprising: inserting a tip of a probe through a membrane of a cell, the tip comprising a first microchannel and a second microchannel; injecting a buffer fluid from the second microchannel, through an opening of the tip, and into the cell, wherein the buffer fluid is miscible with the intracellular material and a portion of the intracellular material diffuses into the buffer fluid to form a zone of combined fluid in the cell; aspirating the combined fluid through the opening and into the first microchannel; intermittently flowing isolator fluid from a third microchannel into the first microchannel to form alternating plugs of combined fluid and isolator fluid, wherein the isolator fluid is immiscible with the combined fluid; and aspirating the alternating plugs through the first microchannel.

32. The method of embodiment 31, wherein the cell is a first cell, and the combined fluid is a first combined fluid, and further comprising: removing the tip from the first cell; inserting the tip into a second cell; injecting the buffer fluid into the second cell, wherein a portion of intracellular material of the second cell diffuses into the buffer fluid to form a zone of second combined fluid in the second cell; aspirating the second combined fluid through the opening and into the first microchannel; and intermittently flowing isolator fluid from the third microchannel into the first microchannel to form alternating plugs of second combined fluid and isolator fluid.

33. The method of embodiment 31, wherein an outer surface of the tip comprises a cavity, the opening comprises a first orifice and a second orifice located at the cavity, the first orifice communicates with the first microchannel and the second orifice communicates with the second microchannel, and wherein the zone is formed at least partially in the cavity.

34. The method of embodiment 31, comprising removing the tip from the cell while leaving a quantity of the buffer fluid remaining in the cell, wherein the buffer fluid comprises a labeling agent.

For purposes of the present disclosure, it will be understood that when a layer (or film, region, substrate, component, device, or the like) is referred to as being "on" or "over" another layer, that layer may be directly or actually on (or over) the other layer or, alternatively, intervening layers (e.g., buffer layers, transition layers, interlayers, sacrificial layers, etch-stop layers, masks, electrodes, interconnects, contacts, or the like) may also be present. A layer that is "directly on" another layer means that no intervening layer is present, unless otherwise indicated. It will also be understood that when a layer is referred to as being "on" (or "over") another layer, that layer may cover the entire surface of the other layer or only a portion of the other layer. It will be further understood that terms such as "formed on" or "disposed on" are not intended to introduce any limitations relating to particular methods of material transport, deposition, fabrication, surface treatment, or physical, chemical, or ionic bonding or interaction. The term "interposed" is interpreted in a similar manner.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample probe, comprising:
a tip comprising a distal end extending along a first direction and configured for penetrating a cellular membrane, an opening located at or proximal to the distal end, and a plurality of tip microchannels extending through the tip and communicating with the opening; and
a body adjoining the tip and comprising a plurality of body microchannels, wherein the body extends along a second direction perpendicular to the first direction, and at least one of the body microchannels communicates with at least one of the tip microchannels,
wherein the plurality of tip microchannels or body microchannels comprises:
a first microchannel comprising a first section and a second section, the first section interconnecting the second section with the opening and having a first characteristic dimension, and the second section having a second characteristic dimension greater than the first characteristic dimension; and
a second microchannel communicating with the first microchannel at or near a junction between the first section and the second section.

2. The sample probe of claim 1, wherein the body is a deflectable cantilever suitable for atomic force microscopy.

3. The sample probe of claim 1, wherein each tip microchannel has a cross-sectional dimension ranging from 0.1 μm to 100 μm.

4. The sample probe of claim 1, wherein the distal end comprises an annular apex circumscribing a cavity extending into the tip, and the opening communicates with the cavity.

5. The sample probe of claim 1, wherein the opening comprises a plurality of orifices, each orifice communicating with at least one of the tip microchannels.

6. The sample probe of claim 1, wherein one of the tip microchannels is a common microchannel interconnecting the opening with at least two other tip microchannels at a junction in the tip.

7. The sample probe of claim 1, comprising a sensor communicating with the first microchannel and configured for producing a signal indicative of a type of fluid passing through the junction.

8. The sample probe of claim 1, comprising a first pump configured for transporting fluid from at least one of the tip microchannels to the opening, and a second pump configured for aspirating fluid from the opening to at least one other tip microchannel.

* * * * *